US008242142B2

(12) United States Patent
Lin et al.

(10) Patent No.: US 8,242,142 B2
(45) Date of Patent: Aug. 14, 2012

(54) CYCLOHEXYLAMINES, PHENYLAMINES AND USES THEREOF

(75) Inventors: Shuo Lin, Los Angeles, CA (US); Zhen Yang, Shenzhen (CN)

(73) Assignees: The Regents of the University of California, Oakland, CA (US); Peking University Shenzhen Graduate School, Guangdong (CN)

( * ) Notice: Subject to any disclaimer, the term of this patent is extended or adjusted under 35 U.S.C. 154(b) by 334 days.

(21) Appl. No.: 12/543,480

(22) Filed: Aug. 18, 2009

(65) Prior Publication Data

US 2010/0048637 A1    Feb. 25, 2010

Related U.S. Application Data

(60) Provisional application No. 61/090,137, filed on Aug. 19, 2008.

(51) Int. Cl.
*A61K 31/4406*    (2006.01)
*C07D 409/12*    (2006.01)

(52) U.S. Cl. .................... 514/337; 546/281.1
(58) Field of Classification Search .......... 514/337; 546/281.1

See application file for complete search history.

(56) References Cited

U.S. PATENT DOCUMENTS

| 6,683,108 B1 | 1/2004 | Baxter et al. |
| 2005/0080138 A1 | 4/2005 | Guicherit et al. |

FOREIGN PATENT DOCUMENTS

| WO | WO 01/74344 | 10/2001 |
| WO | WO 2007/089669 | 8/2007 |
| WO | WO 2008/057468 | 5/2008 |
| WO | WO 2008/057469 | 5/2008 |
| WO | WO 2008/057497 | 5/2008 |

OTHER PUBLICATIONS

International Search Report and Written Opinion for PCT/US09/54328 dated Dec. 10, 2009.
Abdel-Magid et al. "Reductive Amination of Aldehydes and Ketones with Sodium Triacetoxyborohydride. Studies on Direct and Indirect Reductive Amination Procedures," *J. Org. Chem.* 1996, vol. 61, No. 11, pp. 3849-3862.
Chen, J. K. et al., "Small molecule modulation of Smoothened activity," *Proc. Natl. Acad. Sci. U.S.A.*, Oct. 29, 2002, vol. 99, No. 22, pp. 14071-14076.
Chen, J. K. et al., "Inhibition of Hedgehog signaling by direct binding of cyclopamine to Smoothened," *Genes Dev.*, 2002, vol. 16, pp. 2743-2748.
Frank-Kamenetsky, M. et al., "Small-molecule modulators of Hedgehog signaling: identification and characterization of Smoothened agonists and antagonists," *J. Biol.*, vol. I, Issue 2, Article 10, Nov. 6, 2002, 19 pages.
Katoh, Y. et al., "Hedgehog signaling pathway and gastrointestinal stem cell signaling network (Review)," *Int. J. Mol. Med.* 18, Sep. 2006, pp. 1019-1023.
Lee, J. et al., "A small-molecule antagonist of the hedgehog signaling pathway," *Chembiochem*, 2007, vol. 8, pp. 1916-1919.
Nefzi, A. et al., "Solid Phase Synthesis of 1,3,4,7-Tetrasubstituted Perhydro-1,4-Diazepine-2,5-Diones," *Tetrahedron Letters*, 1997, vol. 38, No. 28, 4943-4946.
Rohatgi, R. et al., "Patching the gaps in Hedgehog signaling," *Nat. Cell. Biol.*, Sep. 2007, vol. 9, No. 9, pp. 1005-1009.
Romer, JT et al., "Suppression of the Shh pathway using a small molecule inhibitor eliminates medulloblastoma in Pctl(+/−)p53(−/−) mice," *Cancer Cell*, 2004; vol. 6, pp. 229-240.
Salvatore et al., "Efficient and selective $N$-alkylation of carbamates in the presence of $Cs_2CO_3$ and TBAI," *Tetrahedron Lett.*, 42(10): pp. 1799-1801.
Sasaki, H. et al., "A binding site for Gli proteins is essential for HNF-3beta floor plate enhancer activity in transgenics and can respond to Shh in vitro," *Development 124*, 1997, pp. 1313-1322.

(Continued)

*Primary Examiner* — Taofiq A Solola
(74) *Attorney, Agent, or Firm* — Joseph P. Meara; Foley & Lardner LLP

(57) ABSTRACT

Compounds having the formula I, their methods of synthesis, and pharmaceutically acceptable salts of certain of them are provided in which the variables have the definitions described herein.

Compositions including the compounds having the formula I-A in which the variables have the definitions described herein, and methods of using the compositions for the treatment of certain diseases mediated by the up-regulation of Smo are also disclosed.

19 Claims, 3 Drawing Sheets

OTHER PUBLICATIONS

Shaw, K. J. et al., "Routes to Mitomycins. Chirospecific Synthesis of Aziridinomitosenes," *J. Org. Chem.*, May 1, 1985, vol. 50, No. 23, pp. 4515-4523.

Taipale, J. et al., "Effects of oncogenic mutations in Smoothened and Patched can be reversed by cyclopamine," *Nature*, Aug. 31, 2000, vol. 406, pp. 1005-1009.

Thompson, C. M. et al., "Synthesis, Configuration, and Chemical Shift Correlations of Chiral 1,3,2-Oxazaphospholidin-2-ones Derived from *l*-Serine," *J. Org. Chem.* 1990, vol. 55, No. 1, pp. 111-116.

Wang, N. et al., "A Concise and Diversity-Oriented Approach to the Synthesis of SAG Derivatives," *J. Comb. Chem.* 2008, vol. 10, No. 6, pp. 825-834.

Williams, J. A. et al., "Identification of a small molecule inhibitor of the hedgehog signaling pathway: Effects on basal cell carcinoma-like lesions," *PNAS*, vol. 100, No. 8, Apr. 15, 2003, pp. 4616-4621 and 8607.

Yang, H. et al., "Converse Conformational Control of Smoothened Activity by Structurally Related Small Molecules," *J. Biol. Chem.*, Apr. 14, 2009, vol. 284, 18 pages.

Zhao, Y. et al., "Hedgehog regulates smoothened activity by inducing a conformational switch," *Nature*, Nov. 8, 2007, vol. 450, 8 pages.

SEQUENCE LISTING

```
<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgagctagcg gatccccggg aacagattc                                         29

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgacgcgtt ttaccaacag taccgg                                            26

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggggaacatc tacagtcatc                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtggcagttc gtctcataaa                                                   20

<210> SEQ ID NO 5
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgattgtgac tcctttgg                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tccttattag gggcactg                                                  18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctatgagctg cctgacgg                                                  18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggtggaagg agcaagag                                                  18
```

CYCLOHEXYLAMINES, PHENYLAMINES AND USES THEREOF

CROSS REFERENCE TO RELATED APPLICATION

This application claims priority to U.S. Provisional Application No. 61/090,137, filed Aug. 19, 2008, the entire contents of which are incorporated by reference herein and for all purposes.

FIELD

The present technology relates to low molecular weight compounds, particularly cyclohexylamines and phenylamines, compositions and medicaments thereof, methods of their preparation, and methods of treatment of various diseases using these compounds and compositions.

BACKGROUND

The Hedgehog (Hh) signaling pathway normally functions during embryogenesis to direct cellular differentiation and proliferation and in adult tissue homeostasis, and tissue repair in the presence of chronic inflammation. Mutations in Hh and its downstream signaling components are associated with a number of diseases. For example, aberrant activation of the Hh pathway is involved in certain cancers, including basal cell carcinoma (BCC) and medulloblastoma. Recent results show that inhibitors of Hh signaling induced the regression of medulloblastoma allografts and arrested proliferation of basal cells within BCC-like lesions and led to regression of the lesions.

An important component in the Hh signaling pathway is the seven-pass transmembrane protein Smoothened (Smo). Smo is a downstream activator in the Hh pathway and may be upregulated in certain cancers such as BCC. As such, compounds capable of inhibiting Smo may be useful in treating disorders in which Hh and/or Smo signaling is upregulated. Moreover, Smo inhibitors may also be useful for studying Hh regulated biology.

SUMMARY

There are provided herein compounds, compositions including the compounds, methods of preparing the compounds and compositions, and methods of using the compounds and compositions to treat various diseases, including but not limited to, basal cell carcinoma, medulloblastoma, and certain other solid cancers.

BRIEF DESCRIPTION OF THE DRAWINGS

FIG. 1. Characterization of SANT compounds in zebrafish. Reverse transcription followed by real-time PCR shows the down-regulation of Hh signal pathway target genes mRNA levels after treatment with different concentration of SANT74.

FIG. 2. Conformational Changes of Smo induced by SANT compounds and SAG. Mouse Smo proteins were fused to CFP and YFP at N-terminus, C-terminus and intro-molecularly. FRET was assayed in the absence or presence of Shh with SANT 74, SANT75 and SAG.

DETAILED DESCRIPTION

Figure 1A:
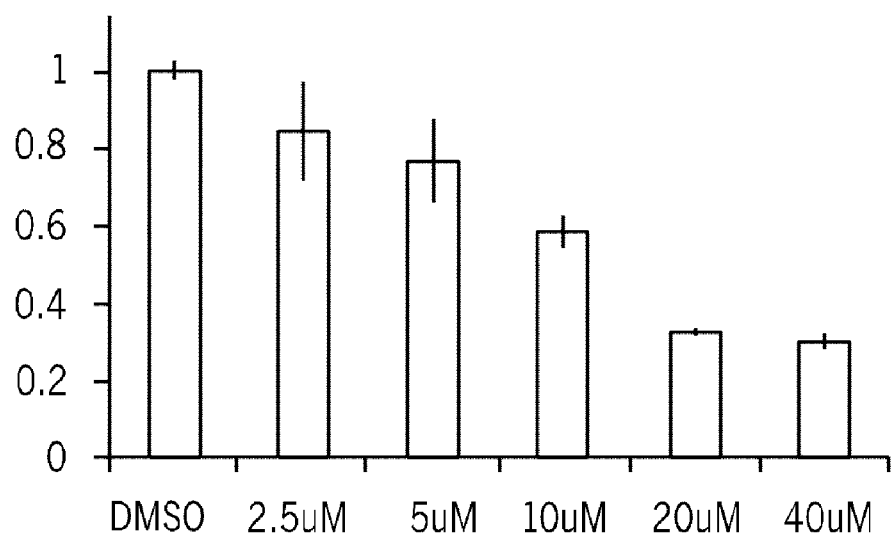
FIGS. 1A and 1B show the Ptch1/beta-actin and Gli1/beta-actin mRNA ratio, respectively.

The following terms are used throughout as defined below.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates, isothiocyanates; cyanates; thiocyanates; imines; nitro groups; nitrites (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, carboxyalkyl, and the like.

Cycloalkyl groups include mono-, bi- or tricyclic alkyl groups having from 3 to 14 carbon atoms in the ring(s), or, in some embodiments, 3 to 12, 3 to 10, 3 to 8, or 3, 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups as described below, and fused rings, such as, but not limited to, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Bridged cycloalkyl groups are cycloalkyl groups in which two or more hydrogen atoms on the same or different carbon atoms are replaced by an alkylene bridge, wherein the bridge can contain 1 to 6 carbon atoms Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Thus, alkenyl groups have from 2 to 12 carbon atoms, and typically from 2 to 10 carbons or, in some embodiments, from 2 to 8, 2 to 6, or 2 to 4 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms Examples of cycloalkenyl groups include cyclohexenyl, cyclopentenyl, cyclohexadienyl, butadienyl, pentadienyl, and hexadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydro furanyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the groups Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H).

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently a substituted or unsubstituted alkyl, alkenyl, alkynyl, cycloalkyl, aryl, aralkyl, heterocyclylalkyl, or heterocyclyl group as defined herein. R$^{33}$ may also be H.

The term "amine" (or "amino") as used herein refers to —NHR$^{35}$ and —NR$^{36}$R$^{37}$ groups, wherein R$^{35}$, R$^{36}$ and R$^{37}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is NH, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{38}$R$^{39}$ and —NR$^3$SO$_2$R$^{39}$ groups, respectively. R$^{38}$ and R$^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$).

The term "thiol" refers to —SH groups, while sulfides include —SR$^{40}$ groups, sulfoxides include —S(O)R$^{41}$ groups, sulfones include —SO$_2$R$^{42}$ groups, and sulfonyls include —SO$_2$OR$^{43}$. R$^{40}$, R$^{41}$, R$^{42}$, and R$^{43}$ are each independently a substituted or unsubstituted alkyl, cycloalkyl alkenyl, alkynyl, aryl aralkyl, heterocyclyl or heterocyclylalkyl group as defined herein.

The term "urea" refers to —$NR^{44}$—C(O)—$NR^{45}R^{46}$ groups. $R^{44}$, $R^{45}$, and $R^{46}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C($NR^{47}$)$NR^{48}R^{49}$ and —$NR^{47}$C($NR^{48}$)$R^{49}$, wherein $R^{47}$, $R^{48}$, and $R^{49}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —$NR^{50}$C($NR^{51}$)$NR^{52}R^{53}$, wherein $R^{50}$, $R^{51}$. $R^{52}$ and $R^{53}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C($R^{54}$)=C($R^{55}$)$NR^{56}R^{57}$ and —$NR^{54}$C($R^{55}$)=C($R^{56}$)$R^{57}$, wherein $R^{54}$, $R^{55}$, $R^{56}$ and $R^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "imide" refers to —C(O)$NR^{58}$C(O)$R^{59}$, wherein $R^{58}$ and $R^{59}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —$CR^{60}$($NR^{61}$) and —N($CR^{60}R^{61}$) groups, wherein $R^{60}$ and $R^{61}$ are each independently hydrogen or a substituted or unsubstituted alkyl, cycloalkyl, alkenyl, alkynyl, aryl aralkyl, heterocyclyl or heterocyclylalkyl group as defined herein, with the proviso that $R^{60}$ and $R^{61}$ are not both simultaneously hydrogen.

The term "protected" with respect to hydroxyl groups, amine groups, carboxy groups, and sulfhydryl groups refers to forms of these functionalities which are protected from undesirable reaction by means of protecting groups. Protecting groups are known to those skilled in the art and can be added or removed using well-known procedures such as those set forth in Protective Groups in Organic Synthesis, Greene, T. W.; Wuts, P. G. M., John Wiley & Sons, New York, N.Y., (3rd Edition, 1999). It is also well known to those skilled in the art that certain protecting groups are removed by contacting with a base while certain other protecting groups are stable to such base treatment but are removed upon contact with an acid. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoyl, formate, acetate, trichloroacetate, and trifluoroacetate.

N-Protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl and other arylmethyl groups, dimethyl (substituting the methylene moiety) and other similar, di and monoalkylated benzyl and arylmethyl groups, diphenylmethyl and other diarylmethyl groups, triphenylmethyl, trityl and other triarylmethyl groups, benzyloxymethyl and the like; and silyl groups such as trimethylsilyl and the like. Typical N-protecting groups include formyl, acetyl, benzoyl, pivaloyl, t-butylacetyl, phenylsulfonyl, benzyl, cumyl (2-phenyl-2-propyl), 9-fluorenylmethyloxycarbonyl (Fmoc), t-butyloxycarbonyl (Boc) and benzyloxycarbonyl (Cbz).

Examples of protected sulfhydryl groups include, but are not limited to, thioethers such as S-benzyl thioether, S-t-butylthioether, and S-4-picolyl thioether; substituted S-methyl derivatives such as hemithio, dithio and aminothio acetals; and others.

Representative carboxy protecting groups are $C_1$ to ($C_8$ alkyl (e.g., methyl, ethyl or tertiary butyl and the like); haloalkyl; alkenyl; cycloalkyl and substituted derivatives thereof such as cyclohexyl, cyclopentyl and the like; cycloalkylalkyl and substituted derivatives thereof such as cyclohexylmethyl, cyclopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aryloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like, alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocyclylcarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(alkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl) methyl and the like.

The term "leaving group" refers to an atom or group of atoms which may be replaced by another atom or group of atoms (e.g., a nucleophile such as an amine, thiol, carbanion, and the like) during a chemical reaction. Illustrative leaving groups are well known in the art and include, but are not limited to halogen groups (e.g., I, Br, F, Cl), substituted and unsubstituted sulfonate groups (e.g., mesylate, tosylate, triflate), substituted and unsubstituted $C_6$-aryloxy groups, substituted and unsubstituted $C_6$-arylacyloxy groups and the like.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereoisomeric or geometric isomeric forms, it should be understood that the present technology encompasses any tautomeric, conformational isomeric, stereoisomeric and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, imidazoles may exhibit the following isomeric forms, which are referred to as tautomers of each other:

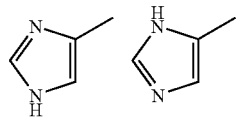

As readily understood by one skilled in the art, a wide variety of functional groups and other structures may exhibit tautomerism, and all tautomers of compounds as described herein are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

According to one aspect, the present technology provides compounds of formula I

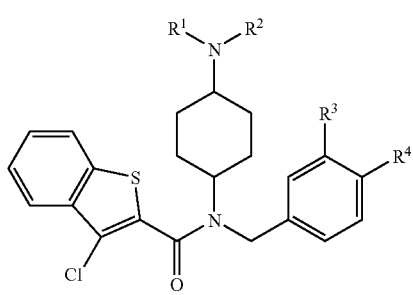

wherein
$R^1$ is hydrogen or an N-protecting group;
$R^2$ is a $C_2$-$C_3$ alkyl, haloalkyl or alkenyl group;
one of $R^3$ and $R^4$ is hydrogen and the other is

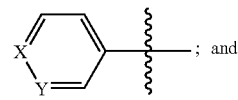

one of X and Y is CH and the other is N; or
a stereoisomer thereof, or a pharmaceutically acceptable salt thereof.

In one embodiment, $R^1$ is hydrogen, and in another embodiment, $R^1$ is an N-protecting group. Suitable N-protecting groups include Boc, Cbz, pivaloyl, acetyl and benzyl. In another embodiment, $R^1$ is an unsubstituted $C_2$-$C_3$ alkyl or unsubstituted $C_1$-$C_3$ alkenyl group. In another embodiment, $R^2$ is an unsubstituted $C_2$-$C_3$ alkenyl group wherein the nitrogen atom bonded to $R^2$ is bonded to an sp3 carbon atom; i.e., the nitrogen atom is not bonded to a vinylic or an sp2 carbon atom. In another embodiment, the present technology provides compounds of formula IA

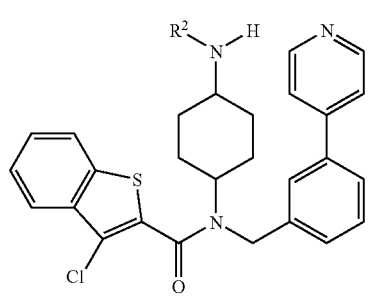

In another embodiment, the present technology provides compounds of formula I-B

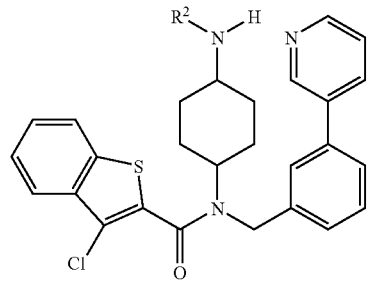
I-B

In another embodiment, the present technology provides compounds of formula I-C

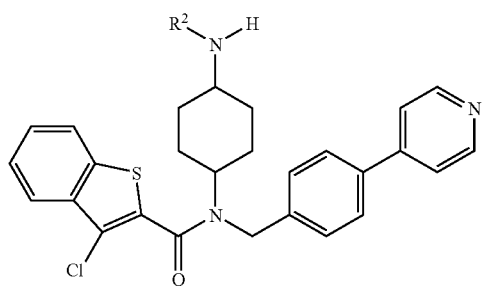
I-C

In another embodiment, the present technology provides compounds of formula I-D

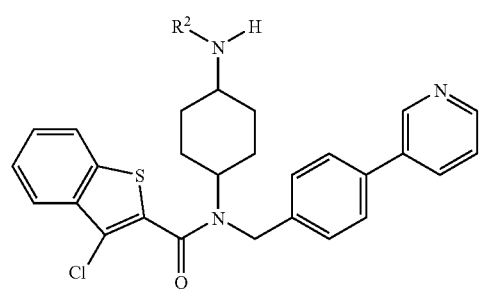
I-D

In another embodiment, the present technology provides compounds of formula I-E

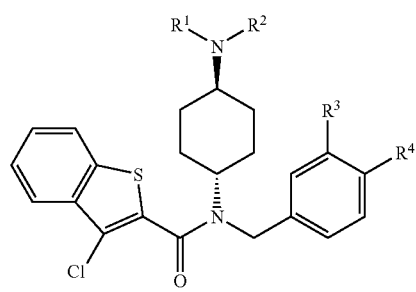
I-E

In another embodiment, the present technology provides compounds of formula I-F

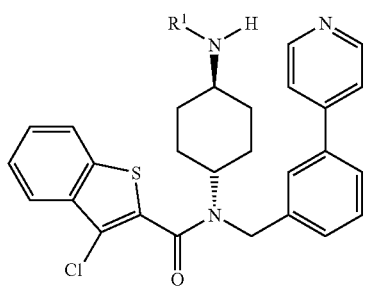
I-F

In formulas I-A to I-F, $R^2$ is defined as in formula I above. In some embodiments, $R^1$ is —$CH_2$—$CH_2$—$CH_3$ or —$CH_2$—$CH$=$CH_2$. In another embodiment, $R^2$ is —$CH_2$—$CH_3$. In another embodiment, the compound is:
3-chloro-N-(trans-4-(propylamino)cyclohexyl)-N-(3-(pyridin-4-yl)benzyl)benzo[b]thiophene-2-carboxamide or
N-(trans-4-(allylamino)cyclohexyl)-3-chloro-N-(3-(pyridin-4-yl)benzyl)benzo[b]thiophene-2-carboxamide, or a pharmaceutically active salt thereof.

In certain other aspects, compounds of the present technology have the formula III

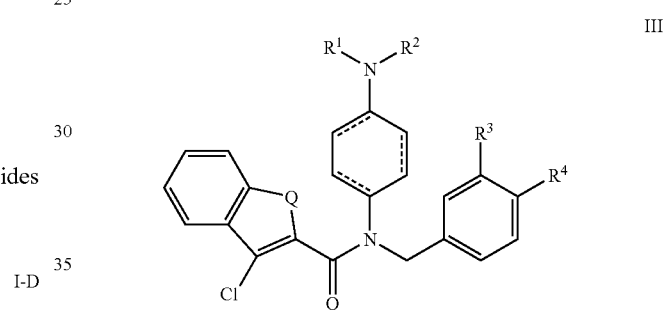
III wherein

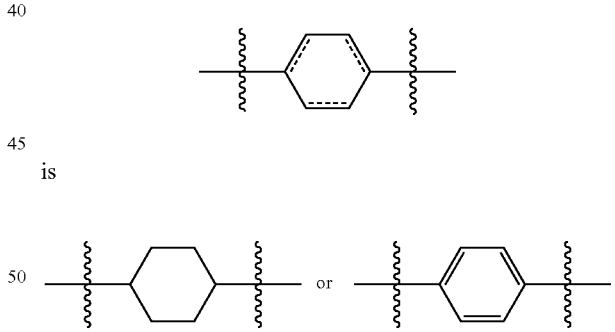

is

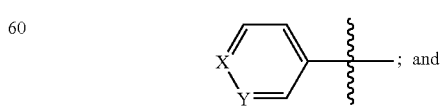

Q is $S(O)_p$ wherein p is 0, 1, or 2, O, or NH;
$R^1$ is hydrogen or an N-protecting group;
$R^{12}$ is $C_2$-$C_3$ alkyl haloalkyl or alkenyl group;
one of $R^1$ and $R^4$ is hydrogen and the other is

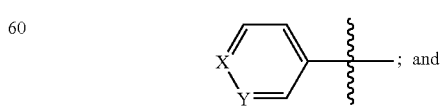
; and one of X and Y is CH and the other is N; or
a stereoisomer thereof, or a pharmaceutically acceptable salt thereof. In one embodiment, p is 0; i.e., Q is S.

According to another aspect, the present technology provides methods of synthesizing compounds of formula I comprising
(i) contacting a compound of formula II-A

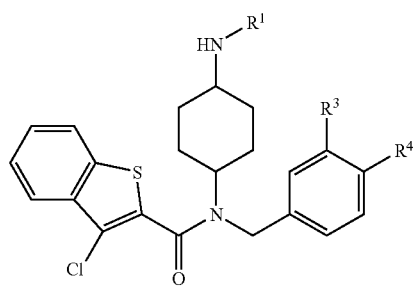

II-A with a base and $R^2$—Z, wherein Z is a leaving group, $R^1$ is an N-protecting group and $R^2$-$R^4$ are defined as in formula I above, to provide the compound of formula I

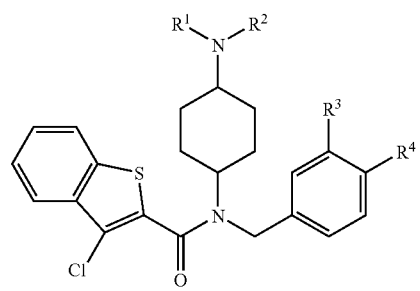

I wherein $R^1$ is an N-protecting group, $R^2$, $R^3$, and $R^4$ are as defined above. In some embodiments, Z is selected from the group consisting of Cl, Br, I, and $OSO_2R^5$ wherein $R^5$ is alkyl haloalkyl, aryl, or heteroaryl. In one embodiment, $R^5$ is methyl, phenyl, 4-methylphenyl, 4-bromophenyl, or trifluoromethyl. In some embodiments, the base is a hydride, such as, e.g., sodium hydride or potassium hydride.

In another embodiment of the present methods, the compound synthesized has formula I-F

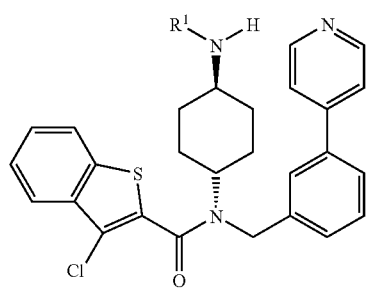

I-F

In another embodiment, $R^2$ is —CH—$CH_3$, $CH_2$—$CH_2$—$CH_3$, or —$CH_2$—CH=$CH_2$. In another embodiment, the N-protecting group of $R^1$ is t-butyloxycarbonyl Boc, Cbz pivaloyl, acetyl or benzyl.

In another embodiment, the method further comprises a second (ii) step of removing the N-protecting group to provide the compound of formula I wherein $R^1$ is hydrogen. In another embodiment, the N-protecting group is removed by contacting the compound of formula I with an acid selected from HCl and $CF_3CO_2H$.

Compounds of the present technology may be synthesized as shown in Scheme 1 below.

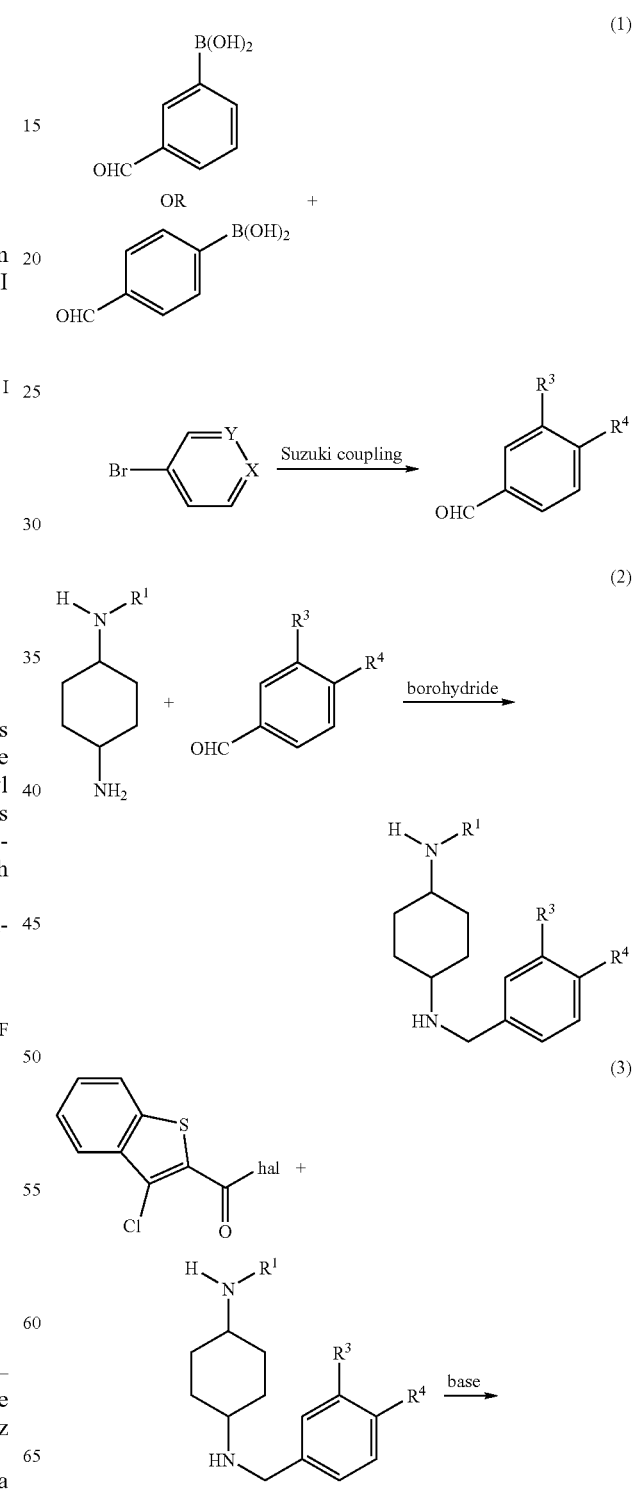

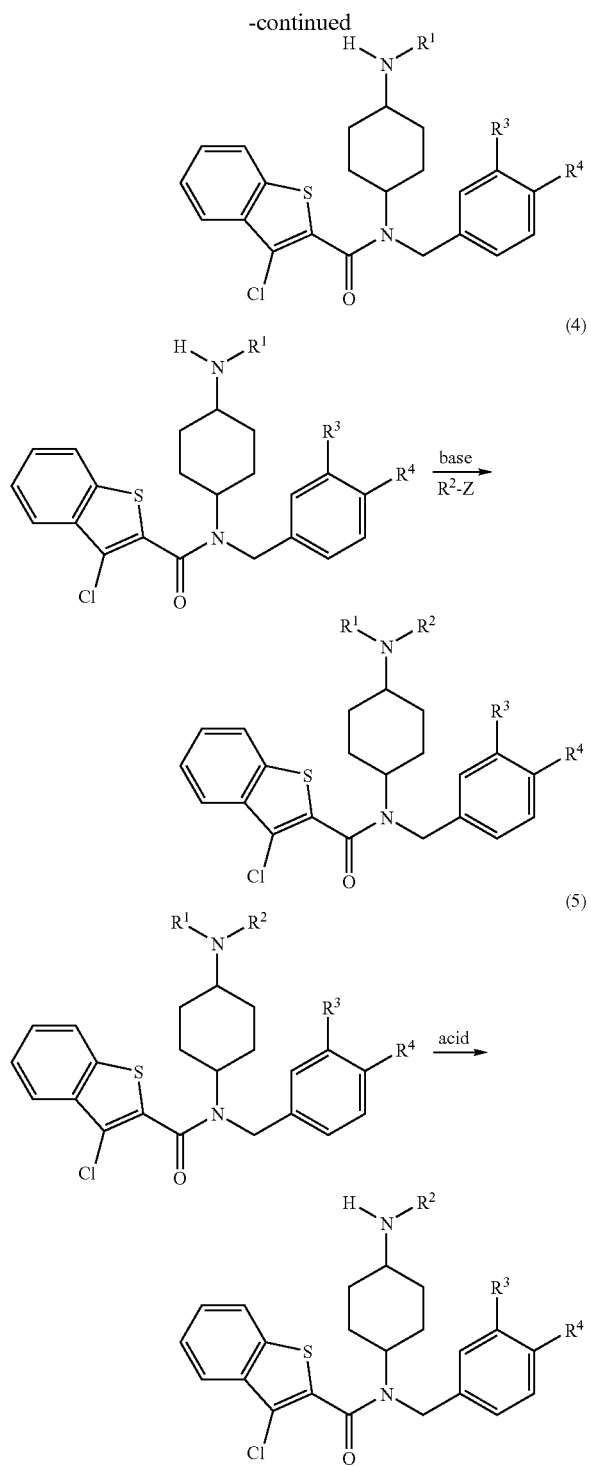

In the scheme, $R^1$-$R^4$, X, Y, and Z are defined as in formula I above, and hal is Cl or Br. According to this scheme, a variety of substituted benzaldehydes may be coupled with the bromo-pyridines and catalyzed by a variety of Pd reagents. Particularly useful as a catalyst is a palladacycle exemplified in the Examples section. A variety of borohydrides are useful in the reductive amination of the aldehyde with the 4-substituted cyclohexylamine. In one embodiment, the borohydride employed is $NaBH_4$. In another embodiment, the borohydride employed is $NaCNBH_3$. $NaBH(OAc)_3$ may also be employed. 4-Substituted arylamines can, similarly be incorporated into the compounds of the present technology by employing a suitable 4-substituted arylamine in step (2). Heteroaryl moieties other than benzothiophene, such as benzofurans or indoles, can similarly be incorporated into the compounds of the present technology, by employing, suitable benzofuran or indole acid halides in step (3).

Steps (4) and (5) are similar to steps (i) and (ii) disclosed above. Thus, with respect to step 4, where $R^2$ is a suitable N-protecting group, the cyclohexylamine (or phenylamine) is deprotonated with a base and treated with $R^2$—Z where $R^2$ and Z are as defined above. Bases that may be used in this reaction include sodium hydride, potassium hydride, LDA (lithium diisopropyl amide), LiHMDS (lithium hexamethyldisilazide), NaHMDS (sodium hexamethyldisilazide), KHMDS (potassium hexamethyldisilazide), or cesium carbonate and tetrabutylammonium iodide (see, Salvatore et al., Tetrahedron Lett., 42(10): 1799-1801, incorporated herein by reference). The resulting alkylated amine may then be deprotected to provide the desired N-alkylamine. Any N-protecting group that withstands the N-alkylation step but is removable without disturbing the rest of the compound may be used. In some embodiments, acid sensitive N-protecting groups including Boc may be used. Other suitable N-protecting groups include Cbz, pivaloyl, acetyl, benzyl, and the like.

The present technology also provides for pharmaceutical compositions and medicaments which may be prepared by mixing one or more compounds of the present technology, prodrugs thereof, pharmaceutically acceptable salts thereof, stereoisomers thereof, tautomers thereof, or solvates thereof, with pharmaceutically acceptable carriers, excipients, binders, diluents or the like to treat certain diseases as described herein. Without being bound by mechanism, certain of these diseases are be characterized by up regulation of Smoothened.

In another aspect, the present technology provides compositions comprising compounds of formulas I (wherein $R^1$ is hydrogen), I-A, I-B, I-C, I-D, and I-F and a pharmaceutically acceptable carrier, excipient, or diluent. In one embodiment, the compound is:
3-chloro-N-(trans-4-(propylamino cyclohexyl)-N-(3-(pyridin-4-yl)benzyl)benzo[b]thiophene-2-carboxamide or
N-(trans-4-(allylamino)cyclohexyl)-3-chloro-N-(3-(pyridin-4-yl)benzyl)benzo[b]thiophene-2-carboxamide.

Such compositions can be in the form of, for example, granules, powders, tablets, capsules, syrup, suppositories, injections, emulsions, elixirs, suspensions or solutions. The instant compositions can be formulated for various routes of administration, for example, by parenteral and oral administration. Parenteral or systemic administration includes, but is not limited to, subcutaneous, intravenous, intraperitoneally, intramuscular injections. The following dosage forms are given by way of example and should not be construed as limiting the instant technology.

Pharmaceutically acceptable salts of the compounds of the present technology are considered within the scope of the present technology. When the compound of the present technology has a basic group, such as, for example, an amino or a substituted amino group, pharmaceutically acceptable salts can be formed with inorganic acids (such as hydrochloric acid, hydroboric acid, nitric acid, sulfuric acid, and phosphoric acid), organic acids (e.g. formic acid, acetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. trimethylamine, triethylamine, pyridine, picoline, ethanolamine, diethanolamine, triethanolamine) or basic amino acids (e.g. arginine, lysine and ornithine).

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical compositions and/or medicament may be a powder suitable for reconstitution with an appropriate solution as described above. Examples of these include, but are not limited to, freeze dried, rotary dried or spray dried powders, amorphous powders, granules, precipitates, or particulates For injection, the pharmaceutical compositions may optionally contain stabilizers, pH modifiers, surfactants, bioavailability modifiers and combinations of these.

For oral, buccal, and sublingual administration, powders, suspensions, granules, tablets, pills, capsules, gelcaps, and caplets are acceptable as solid dosage forms. These can be prepared, for example, by mixing one or more compounds of the present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical compositions and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension pharmaceutical compositions may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension pharmaceutical compositions.

Besides those representative dosage forms described above, pharmaceutically acceptable excipients and carriers are generally known to those skilled in the art and are thus included in the present technology. Such excipients and carriers are described, for example, in "Remingtons Pharmaceutical Sciences" Mack Pub. Co., New Jersey (1991), which is incorporated herein by reference.

The pharmaceutical compositions of the present technology may be designed to be short-acting, fast-releasing, long-acting, and sustained-releasing as described below. Thus, the pharmaceutical compositions may also be prepared for controlled release or for slow release.

The instant compositions may also comprise, for example, micelles or liposomes, or some other encapsulated form, or may be administered in an extended release form to provide a prolonged storage and/or delivery effect. Therefore, the pharmaceutical compositions and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing therapeutically effective amounts are well within the bounds of routine experimentation and therefore, well within the scope of the present technology.

In another aspect, the present technology provides a method of treatment comprising administering a therapeutically effective amount of a composition comprising a compound of formula I (wherein $R^1$ is hydrogen), I-A, I-B, I-C, I-D, or I-F. In another embodiment, the compound administered is 3-chloro-N-(trans-4-(propylamino)cyclohexyl)-N-(3-(pyridin-4-yl)benzyl)benzo[b]thiophene-2-carboxamide or N-(4-(trans-allylamino)cyclohexyl)-3-chloro-N-(3-(pyridin-4-yl)benzyl)benzo[b]thiophene-2-carboxamide or a pharmaceutically acceptable salt thereof.

Without being bound by mechanism, certain compounds of the present technology, for example, those useful in the treatment methods of the present technology, are capable of inhibiting Smoothened. Thus, in certain treatment method embodiments of the present technology, the disease treated is mediated, at least in part, by Smoothened. In certain other embodiments, the disease treated is characterized by an up-regulation of Smoothened.

Treatment within the context of the instant technology, means an alleviation, in whole or in part, of symptoms associated with a disorder or disease, or slowing or halting of further progression or worsening of those symptoms, or tending to prevent or ward off the disease or disorder in a subject at risk for developing the disease or disorder. Such disease or disorders include, but are not limited to basal cell carcinoma, medulloblastoma, and certain solid cancers where Hh signaling and/or Smoothened is upregulated.

For example, within the context of treating diseases including a Hh and/or Smoothened mediated disorder, a successful treatment may include an alleviation of symptoms or slowing or halting the progression of the disease, as measured by a reduction in the Smoothened levels or activation. As used herein, a "therapeutically effective amount" of a compound of the technology refers to an amount of the compound that alleviates, in whole or in part, symptoms associated with a disorder or disease, or slows or halts of further progression or worsening of those symptoms, or prevents or provides prophylaxis for the disease or disorder in a subject at risk for developing the disease or disorder. A subject is any animal that can benefit from the administration of a compound as disclosed herein. In some embodiments, the subject is a mammal, for example, a human, a primate, a dog, a cat, a horse, a cow, a pig, a rodent, such as for example a rat or mouse. Typically, the mammal is a human.

A therapeutically effective amount of a compound of the present technology or a pharmaceutically acceptable salt thereof may vary depending upon the route of administration and dosage form. Effective amounts of the compounds of the present technology, or pharmaceutically acceptable salts thereof typically fall in the range of about 0.0011 up to 1100 mg/kg/day, and more typically in the range of about 0.05 up to 25 mg/kg/day. Typically, the compound or compounds of the present technology are selected to provide a pharmaceutical composition that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

In particular, the following papers are herein incorporated by reference in their entireties: Yang, H., et al. "Converse Conformational Control of Smoothened Activity by Structurally Related Small Molecules," *J. Biol. Chem.* (2009), 284, 20876-884; Wang, N., et al. "A Concise and Diversity-Oriented Approach to the Synthesis of SAG Derivatives" *J. Comb. Chem.* (2008) 10, 825.

The present technology, thus generally described, will be understood more readily by reference to the following examples, which are provided by way of illustration and are not intended to be limiting of the present technology.

EXAMPLES

The following, abbreviations are used throughout the present disclosure with respect to chemical and biological terminology:

μL: Microliter
Ac: Acetyl
ATP: Adenosine triphosphate
Bloc: Tertiarybutyloxycarbony ($Me_3C$—O—CO—)
Bn: Benzyl
CFP: Cyan fluorescent protein
DCM: Dichloromethane
DMEM: Dulbecco's Modified Eagle Medium
DMF: Dimethylformamide
DMSO: Dimethylsulfoxide
Et: Ethyl
GC-MS: Gas chromatography-mass spectrometry
HRMS: High resolution mass spectroscopy
ESI: Electrospray ionization
GFP: Green fluorescent protein
hpf: hours post fertilization
iBu: Isobutyl
iPr: Isopropyl
IR: Infra red
J: NMR coupling constant between hydrogens
Me: Methyl
mg: Milligram
MHz: Megahertz
mL: Milliliter
mmol: Millimoles
MS (EI): Mass spectroscopy (electron impact)
NMR: Nuclear magnetic resonance
PE: Petroleum ether
Ph: Phenyl
rt: Room temperature
TFA: Trifluoroacetic acid
THF: Tetrahydrofuran
TMS: Trimethylsilyl
YFP: Yellow fluorescent protein General Procedures All reactions were carried out under a nitrogen atmosphere with dry solvents under anhydrous conditions, unless otherwise noted. All the chemicals were purchased commercially, and used without further purification. Anhydrous THF and diethyl ether were distilled from sodium-benzophenone, and dichloromethane was distilled from calcium hydride. The boiling point of petroleum ether is between 60-90° C. Yields refer to chromatographically, unless otherwise stated. Reactions were monitored by thin-layer chromatography (TLC) carried out on silica gel plates (60F-254) using UV light as visualizing agent and an ethanolic solution of phosphomolybdic acid and cerium sulfate, and heat as developing agents. Silica gel (60, particle size 0.040-00.63 mm) was used for flash column chromatography. Control compound SAG was synthesized according to the method of Chen et al., supra, or by the alkylation method of the present technology employing methyl iodide as the electrophile.

Example I

Synthesis of the Compounds of the Present Technology

As shown in Scheme 2, the synthesis started with coupling of intermediates 6 and 10 together in methanol in the presence of 4 Å molecular sieves. The resultant imine was then reduced by $NaBH_4$ to give product 18 through a direct reductive amination (see, e.g., (a) Abdel-Magid, A. F.; Carson, K. G.; Harris, B. D.; Maryanoff, C. A.; Shah, R. D. J. Org. Chem. 1996, 61, 3849; (b) Shaw, K. J.; Luly J. R.; Rapoport, H. J. Org. Chem. 1985, 50, 4515; (c) Thompson, C. M.; Frick, J. A.; Green, D. L. C. J. Org. Chem. 1990, 55, 111; (d) Nefzi, A.; Ostresh, J. M.; and Houghten, R. A. Tetrahedron Lett. 1997, 38, 4943; incorporated herein by reference) as described by Beachy and his co-workers (Chen, J. K.; Talpale, J.; Young, K. E.; Maltl, T.; Beachy, P. A. Proc. Natl. Acad. Sci. USA, 2002, 99, 14071, incorporated herein by reference). However, applications of this reaction to the preparation of compound 18 are less satisfactory, providing the product in only ca. 50% yield. Therefore, a variety of reaction conditions were screened, and interestingly it turned out that full conversion of 6 and 10 to imine could be achieved simply by mixing them in methanol at room temperature for half an hour without adding any molecular sieves. This process was evidenced by the observation of the disappearance of a carbonyl peak at 191 ppm, and the occurrence of an imine's signal at 158 ppm in a real time $^{13}C$ NMR study. As a result, compound 18 could be eventually made in 95% yield by addition of $NaBH_4$ to the reaction mixture generated by mixing amine 6 with aldehyde if in methanol for 30 min.

Scheme 2

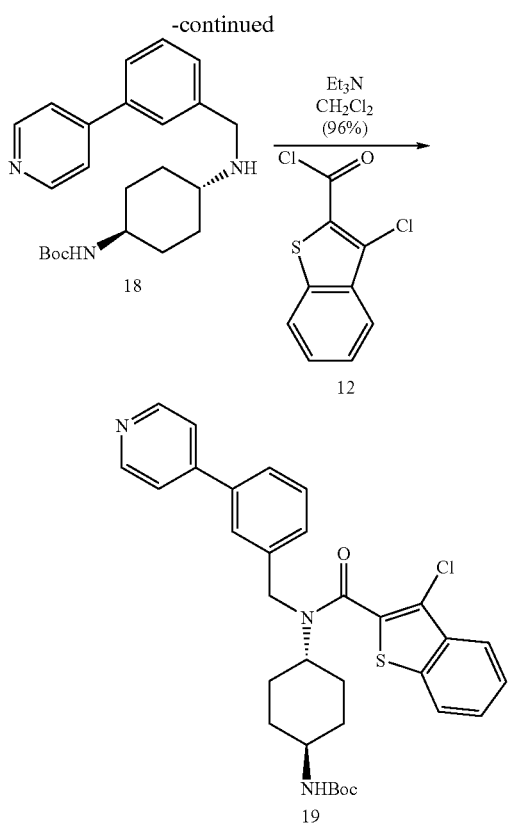

With a successful reductive amination procedure, the consequent secondary amine 18 was treated with acyl chloride 12 in CH$_2$Cl$_2$ with TEA as the base. 96% yield of the desired product 19 was obtained.

To introduce the biaryl subunit, the Pd-catalyzed Suzuki coupling reaction of commercially available aldehyde substituted arylboronic acids and Pyridinyl bromides (see Table 1) was evaluated. Although Pd(PPh$_3$)$_4$ is frequently utilized in the Suzuki reaction, most Suzuki couplings need degassed solvents, and the reactions have to be carried out in an inert atmosphere to avoid oxidative Pd-aggregation, which was observed when the synthesis of compound 10 was attempted under aerobic conditions (for selected Suzuki coupling reactions, see: (a) Chen, H.; Deng, M. Z. Org. Lett. 2000, 2, 1649; (b) Sava, X.; Ricard, L. Mathey, F.; Le Floch, P. Organometallics 2000, 19, 4899; (C) Frank, S. A.; Chen, H.; Kunz, R. K.; Schnaderbeck, M. J.; Roudh, W. R. Org. Lett. 2000, 2, 2691; (d) Leblond, C. R.; Andrews, A. T.; Sun, Y. K.; Sowa, Jr. J. R. Org. Lett. 2001, 3, 1555; (e) Yamada, Y. M. A.; Takeda, K.; Takahashi, H.; Ikegami, S. Org. Lett. 2002, 4, 3371; (f) Parry, P. R.; Wang, C. S.; Batsanov, A. S.; Bryce, M. R.; Tarbit, B. J. Org. Chem. 2002, 67, 7541; (g) Dubbaka, S. R.; Vogel, P. Org. Lett. 2004, 6, 95; (h) Dai, M.; Liang, B.; Wang, C, You, Z.; Xiang, J.; Dong, G.; Chen. J.; Yang, Z. Adv. Synth. Catal. 2004, 346, 1669; incorporated herein by reference). The moisture-stable carbothioamide-derived palladacycle A (Table 1), catalyzed the Suzuki reaction under aerobic conditions (Xiong, Z.; Wang, N.; Dai, M.; Li, Ang, Chen, J.; Yang, Z. Org. Lett. 2004, 6, 3337; incorporated herein by reference. The Suzuki reactions could be carried out in air at 100° C. for 2 h with K$_2$CO$_3$ as base in the presence of palladacycle A as catalyst (1.0 M stock solution in MDAc, less than 0.5 mmol %) and all the reactions gave good results as illustrated in Table 1. The stock solution of palladacycle A could be stored at room temperature over a month without loss of its catalytic activity.

TABLE 1

Parallel synthesis of biaryl molecules by palladacycle A catalyzed Suzuki Coupling Reactions

| entry | Ar$^1$ | Ar$^2$ | t(h) | Pd(mol %) | product | yield |
|---|---|---|---|---|---|---|
| 1 | pyridinyl | phenyl-CHO | 2 | 0.1 | 10a | 86 |
| 2 | pyridinyl | phenyl-CHO | 2 | 0.1 | 10b | 83 |

TABLE 1-continued

Parallel synthesis of biaryl molecules by palladacycle A catalyzed Suzuki Coupling Reactions $$Ar^1Br + Ar^2B(OH)_2 \xrightarrow[\text{DMAc, H}_2\text{O, K}_2\text{CO}_3]{A\ (0.1\text{-}0.5\ \text{mol \%})}_{100°\ C.} Ar^1\text{—}Ar^2$$

| entry | Ar¹ | Ar² | t(h) | Pd(mol %) | product | yield |
|---|---|---|---|---|---|---|
| 3 | 4-pyridyl | 4-CHO-phenyl | 2 | 0.1 | 10c | 79 |
| 4 | 4-pyridyl | 2-methyl-phenyl-CHO | 2 | 0.1 | 10d | 90 |
| 5 | 2-pyridyl | 3-CHO-phenyl | 2 | 0.1 | 10e | 91 |
| 6 | 2-pyridyl | 4-CHO-phenyl | 2 | 0.1 | 10f | 89 |
| 7 | 3-pyridyl | 2-methyl-phenyl-CHO | 2 | 0.1 | 10g | 87 |

[a]Reaction conditions: Ar¹Br (1 mmol). Ar²B(OH)₂ (1.2 mmol) and K₂CO₃ (2 mmol) in a solution of 25% DMAc water solution (2 mL) at 100° C.;
[b]Isolated yield.

The reductive amination for the synthesis of secondary amine 18a-g from their corresponding biaryl aldehydes and amines were evaluated thereafter. To this end, alkyl amine 6 and aryl amine 6a were reacted with biaryl aldehydes 10 and 10a-c, respectively, under the optimized conditions described above. The selected reactions gave the expected secondary amines 18a-g in excellent yields (Table 2).

TABLE 2
Selective reductive amination to form secondary amines
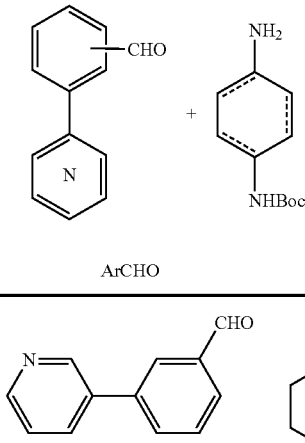
| entry | ArCHO | amine | product | yield (%) |
|---|---|---|---|---|
| 1 |  10a | 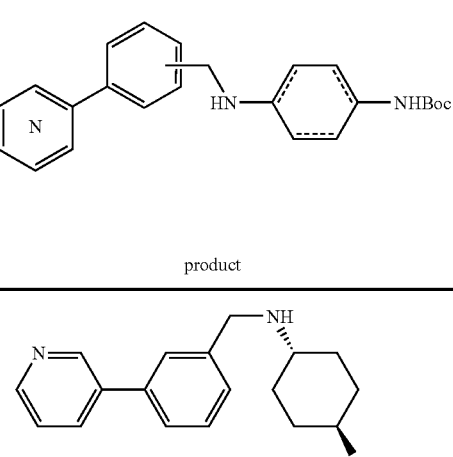 6 | 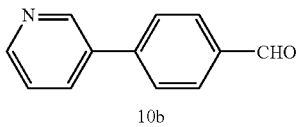 18a | 95 |
| 2 | 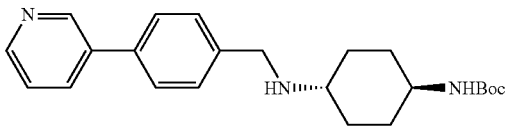 10b | 6 | 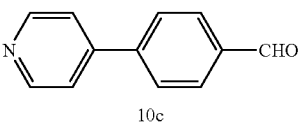 18b | 93 |
| 3 | 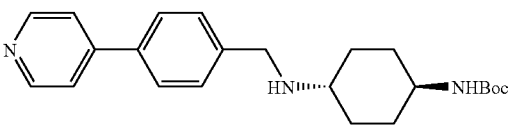 10c | 6 | 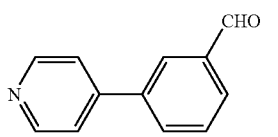 18c | 96 |
| 4 | 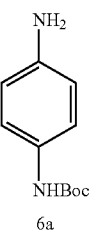 10 | 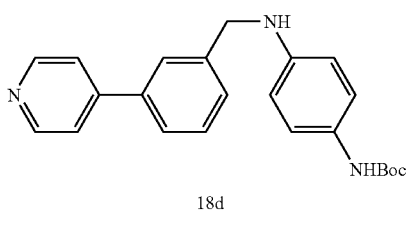 6a | 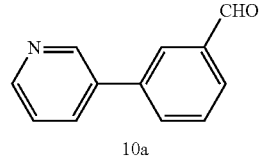 18d | 93 |
| 5 | 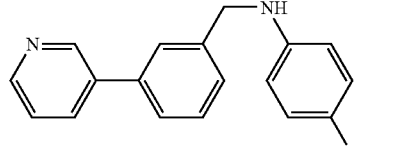 10a | 6a | 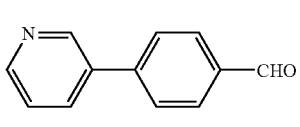 18e | 95 |
| 6 | 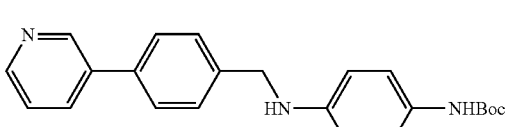 10b | 6a |  18f | 93 |

TABLE 2-continued

Selective reductive amination to form secondary amines

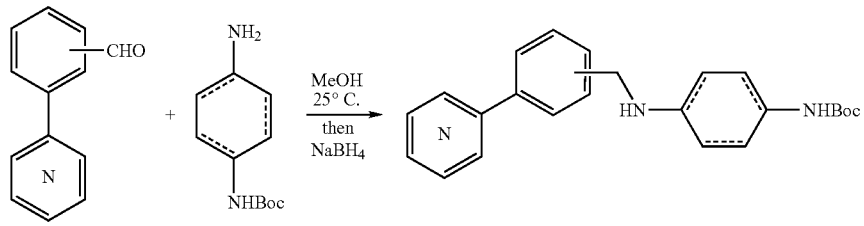

| entry | ArCHO | amine | product | yield (%) |
|---|---|---|---|---|
| 7 | 10c | 6a | 18g | 94 |

<sup>a</sup>Reaction conditions: ArCHO (3.0 mmol), amine (3.3 mmol) in MeOH for 30 min. then NaBH$_4$ (4.5 mmol) at 25° C. for 10 min;
<sup>b</sup>Isolated yield The amide formation by reaction of acyl chlorides 12,12a-b with amines 18a-d and 18f-g were tested. Since benzo[b]furan can be regarded as benzo[b]thiophene isoster, derivatives were made replacing of benzo[b]thiophene with benzo[b]furan. In the event, the secondary amines 18a-d, 18f-g were selected to react with the freshly generated acyl chlorides 12, 12a-b (derived by the treatment of the corresponding carboxylic acid with distilled thionyl chloride in C$_2$Cl$_2$ at 40° C. for 2 h) in the presence of triethylamine at room temperature for 30 min and the expected amides 19a-h were formed in good to excellent yields as illustrated in Table 3.

TABLE 3

Amide bond formation

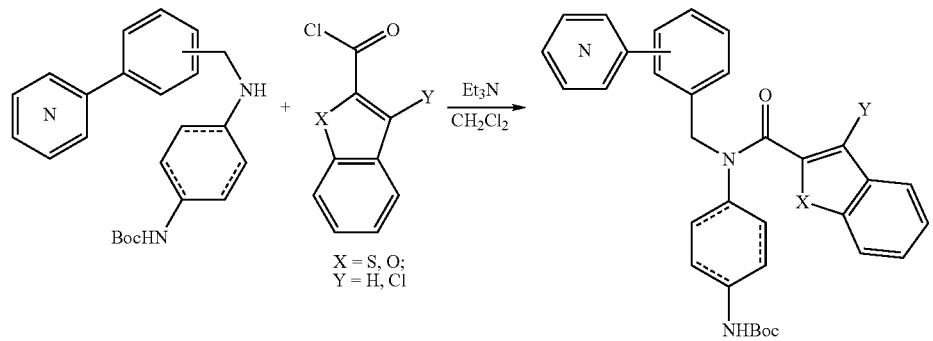

| entry | amine | acyl chloride | product | yield (%) |
|---|---|---|---|---|
| 1 | 18a | 12 | 19a | 96 |

TABLE 3-continued

Amide bond formation

| 2 | 18b | 12a | 19b | 93 |
| 3 | 18a | 12a | 19c | 94 |
| 4 | 18c | 12a | 19d | 93 |
| 5 | 18d | 12 | 19e | 96 |

TABLE 3-continued
Amide bond formation
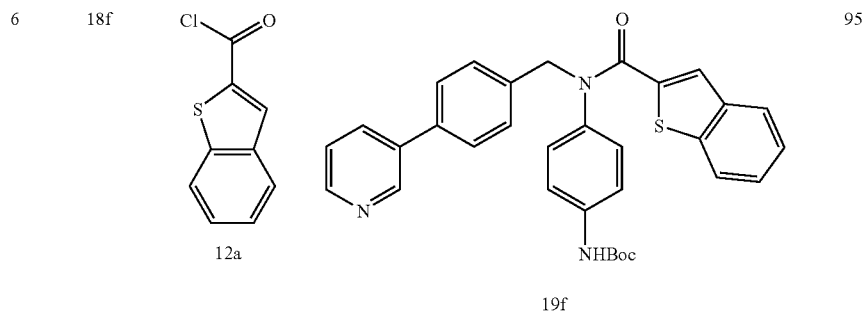
6  18f  ...  19f  95
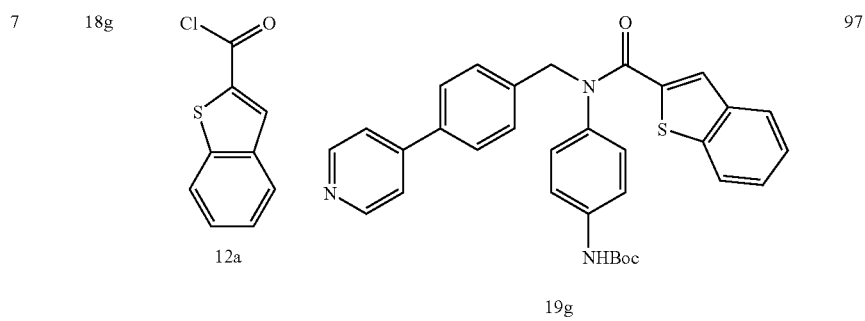
7  18g  ...  19g  97
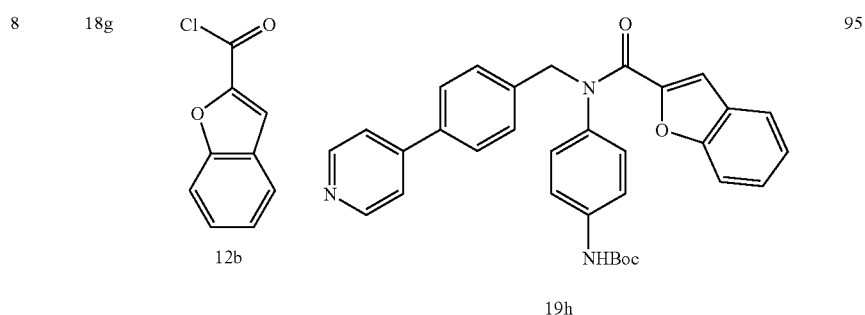
8  18g  ...  19h  95
[a] Reaction conditions: amine (1.9 mmol), acycl chloride (1.1 mmol) and Et$_3$N (2.9 mmol) in CH$_2$Cl$_2$ at 25° C. for 30 min;
[b] Isolated yield.
To evaluate the generality and robustness of direct N-alkylation of carbamate, ethyl-, propyl-, butyl- and allylic halides were employed in the alkylation reactions.

TABLE 4
Synthesis of Compounds of the technology
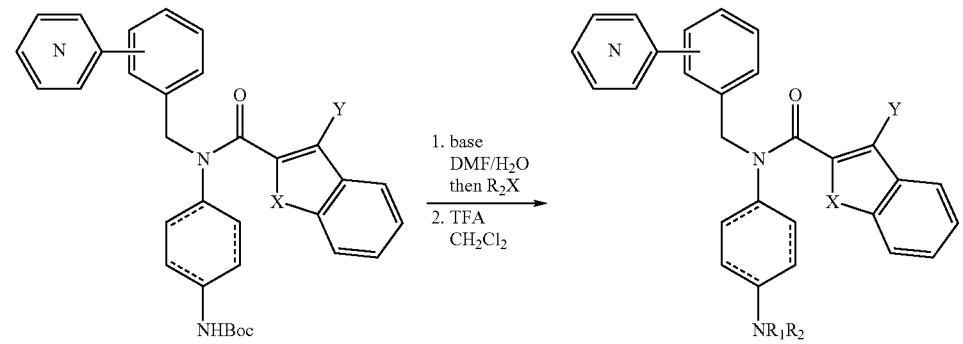
X = O, S;
Y = H, Cl
A: $R_1$ = Boc; $R_2$ = $CH_3$, $C_2H_5$, $C_3H_5$, $C_3H_7$, $C_4H_9$
B: $R_1$ = H, $R_2$ = $CH_3$, $C_2H_5$, $C_3H_5$, $C_3H_7$, $C_4H_9$
| entry | starting material | product A | yield (%)[a] | product B | yield (%)[b] |
|---|---|---|---|---|---|
| 1 | 19 | 20a | 94 | 21a | 94 |
| 2 | 19 | 20b | 96 | 21b | 94 |
| 3 | 19h | 20c | 94 | 21c | 90 |

TABLE 4-continued

Synthesis of Compounds of the technology

| 4 | 19h | [structure 20d] | 95 | [structure 21d] | 93 |
| 5 | 19h | [structure 20e] | 95 | [structure 21e] | 94 |

[a]Isolated yield with semi-preparative HPLC performed on a Agilent 1100 series machine with XDB-C18 (250 × 9.4 mm) column 100% CH$_3$CN, 3 mL/min).
[b]Isolated yield with a flash chromatography on silica gel Five organohalides were reacted with amides 19 and 19h, individually and all the reactions gave the desired products in excellent yields of (see Table 4), indicating that our identified reaction conditions are quite general to make structurally diverse alkylated amines. To complete the synthesis, cleavage of the Boc protecting group was carried out by treatment amides 20a-e with TFA in CH$_2$Cl$_2$ at 0 (C for 1 h to give the desired products 21a-e in high yields (Table 4).

Preparation of (4-amino-cyclohexyl)-carbamic acid tert-butyl ester (6): A solution of Boc$_2$O (1.0 g, 4.6 mmol) in methanol (25 mL) was slowly added to trans-1,4-diaminocyclohexane (1.0 g, 8.8 mmol) in methanol (100 mL), and the reaction mixture was stirred at room temperature for 1 h. After filtration, the filtrate was concentrated under vacuum to ca. 5 mL, and then cooled to −20° C. The crystallized product was collected. The filtrate was resubmitted to the same reaction condition. After the second cycle the desired product 6 was obtained in 56% yield (1.05 g). IR (cm$^{-1}$): 3365, 2933, 1686, 1520; $^1$H NMR (300 MHz, CDCl$_3$): 4.90-5.02 (br, 1H), 3.30-3.42 (br, 1H), 2.58-2.66 (m, 1H), 1.92-2.00 (br, 2H), 1.85-1.97 (m, 4H), 1.43 (s, 9H), 1.10-1.25 (m, 4H); $^{13}$C NMR (75 MHz, CDCl$_3$): 154.0, 77.9, 48.7, 48.0, 34.2, 34.1, 31.0, 30.9, 27.3; MS (EI) calcd for C$_{11}$H$_{22}$N$_2$O$_2$(M$^+$) 214, found 214.

Preparation of 3-pyridin-4-yl-benzaldehyde (10): To a solution of 4-bromopyridine hydrochloride (533.4 mg, 2.7 mmol) in water (4.0 mL) and toluene (4.8 mL) was added slowly a solution of Na$_2$CO$_3$ (714 mg, 6.7 mmol) in water (7.0 mL) at room temperature. The solution was then mixed with 3-formylbenzeneboronic acid (431 mg, 2.9 mmol), Pd(PPh$_3$)$_4$ (100 mg, 0.086 mmol). The reaction mixture was stirred at 85° C. for 24 h, and then cooled to room temperature. The reaction was worked up by extraction of the mixture with CH$_2$Cl$_2$ (4×5 mL). The combined organic phase was dried over anhydrous Na$_2$SO$_4$. The solvent was removed under vacuum, and the residue was purified by a flash chromatography (silica gel, petroleum ether/EtOAc=¼) to give product 10 (420 mg) in 85% yield; $^1$H NMR (300 MHz, CDCl$_3$): 10.1 (s, 1H), 8.72-8.74 (m, 2H), 8.17 (s, 1H), 7.90-7.99 (m, 2H), 7.69 (t, J=11.4 Hz, 1H), 7.57 (d, J=6.6 Hz, 2H); $^{13}$C NMR (75 MHz CDCl$_3$): δ191.5, 150.3, 146.5, 138.8, 136.8, 132.5, 130.1, 129.6, 127.5, 121.3; HRMS (ESI) calcd for C$_{12}$H$_9$NO (M. Hi) 184.07569; found 184.07538.

Preparation of [4-(3-pyridine-4-yl-benzylamino)-cyclohexyl]-carbamic acid tert-butyl ester (18): To a solution of 3-pyridinyl benzaldehyde (10) (205 mg, 1.1 mmol) in methanol (20 ml) was added NT-Boc-1,4-diaminocyclohexane (6) (300 mg, 1.4 mmol), and the mixture was stirred at room temperature for 30 min. To this solution was added NaBH$_4$ (0.5 g, 13.2 mmol) in portions at 0° C., and the reaction mixture was stirred at room temperature overnight. The reaction was worked up by addition of saturated aqueous Na$_2$CO$_3$ (2 ml), and the mixture was then extracted with chloroform (3×6 ml). The combined organic layers were dried over anhydrous MgSO$_4$. The solvent was removed under vacuum and the residue was purified by a flash chromatography on silica gel (CH$_2$Cl$_2$/MeOH=10/1) to give 18 (398 mg) in 95% yield; $^1$H NMR (300 MHz, CDCl$_3$): 8.66 (d, J=8.1 Hz, 2H), 7.39-7.61 (m, 6H), 4.30-4.50 (br, 1H), 3.88 (s, 2H), 3.30-3.50 (br, 1H), 2.40-2.60 (m, 1H), 1.90-2.10 (m, 4H), 1.70-1.90 (br, 1H), 1.44 (s, 9H), 1.06-1.40 (m, 4H) $^{13}$C NMR (75 MHz, CDCl$_3$): 155.2, 150.0, 148.3, 141.5, 138.1, 129.1, 128.7, 126.6, 125.5, 121.6, 79.0, 55.6, 51.0, 49.4, 31.9, 28.3; HRMS (ESI) calcd for C$_{23}$H$_{31}$N$_3$O$_2$ (M+H$^+$) 382.24890; found 382.24896.

Preparation of {4-[(3-chloro-benzo[b]thiophene-2-carbonyl)-(3-pyridin-4-yl-benzyl)-amino]-cyclohexyl}-carbamic acid tert-butyl-ester (19): To a solution of 18 (410 mg, 1.1 mmol) and Et$_3$N (280 μL, 2.0 mmol) in CH$_2$Cl$_2$ (10 mL) was added 3-chlorobenzo[b]thiophene-2-carbonyl chloride 12 (278 mg, 1.2 mmol), and the reaction mixture was stirred at room temperature for 0.5 h. The solvent was removed and the residue was purified by a flash chromatography on silica gel (acetone/PE=5:1) to give the desired product 19 (587 mg) in 96% yield; $^1$H-NMR (400 MHz, CDCl$_3$): 8.65 (br, 2H), 7.20-8.20 (m, 10H), 3.70-5.00 (m, 4H), 3.20-3.40 (br, 1H), 1.75-2.20 (m, 4H), 1.42-1.75 (br, 2H), 1.38 (s, 9H), 0.90-1.30 (br, 2H); $^{13}$C NMR (100 MHz, CDCl$_3$): 163.7, 155.1, 150.2, 148.1, 147.7, 139.2, 138.4, 137.2, 135.6, 130.0, 129.3, 127.6, 126.5, 126.2, 125.5, 122.7, 122.5, 121.6, 119.0, 79.2, 58.7, 48.5, 45.1, 32.1, 30.5, 29.7, 29.3, 28.3; HRMS (EI) calcd for C$_{32}$H$_{34}$ClN$_3$O$_3$S (M$^+$) 575.2009; found 575.2018.

General procedure for preparation of 18a-18g: To a solution of pyridinyl benzaldehyde (10a-c) (1.0 mmol) in methanol (15 mL) was added 6-6a (1.1 mmol), and the mixture was stirred at room temperature for 30 min. To this solution was added NaBH$_4$ (100 mg, 2.5 mmol) in portion at 0° C. and the mixture was stirred at room temperature for 1 h. The reaction was worked up by addition of a saturated aqueous Na$_2$CO$_3$ (2 mL), and the mixture was then extracted with chloroform (3×6 mL), and the combined organic layer was dried over anhydrous Na$_2$SO$_4$. The solvent was removed under vacuum and the residue was purified by a flash chromatography on silica gel (CH$_2$Cl$_2$/MeOH=10/1) to give compound 18a-18g.

Preparation of [4-(3-pyridin-3-yl-benzylamino)-cyclohexyl]-carbamic acid tert-butyl ester (18a): Product 18a (361 mg) was obtained in 95% yield; $^1$H-NMR (300 MHz, CDCl$_3$): 8.82 (d, J=2.1 Hz, 1H), 8.56 (d, J=4.5 Hz, 1H), 7.87 (d, J=7.8 Hz, 1H), 7.54 (s, 1H), 7.31-7.44 (m, 4H), 4.30-4.40 (br, 1H), 3.86 (s, 2H), 3.30-3.50 (br, 1H), 2.40-2.56 (m, 1H), 1.92-2.08 (in 4H), 1.42 (s, 9H), 1.09-1.25 (m, 4H); $^{13}$C NMR (75 MHz CDCl$_3$): 155.1, 148.3, 148.1, 140.7, 137.9, 1360.4, 134.3, 129.1, 127.9, 126.9, 125.8, 123.4, 79.0, 55.5, 50.8, 49.3, 31.8, 31.6, 28.3; MS (EI) calcd for C$_3$H$_{31}$N$_3$O$_2$ (M$^+$) 381; found 381.

Preparation of [4-(4-pyridin-3-yl-benzylamino)-cyclohexyl]-carbamic acid tert-butyl ester (18b): Product 18b (358 mg) was obtained in 93% yield; $^1$H-NMR (300 MHz, CDCl$_3$): 8.81-8.82 (m, 1H), 8.55 (dd, J$_1$=4.5, J$_2$=1.5, 1H), 7.82-7.86 (m, 1H), 7.52 (dd, J$_1$=6.3, J$_2$=1.8, 2H), 7.31-7.44 (m, 3H), 4.30-4.40 (br, 1H), 3.83 (s, 2H), 3.65-3.78 (br, 1H), 3.30-3.50 (br, 1H), 2.40-2.56 (m, 1H), 1.92-2.08 (m, 4H), 1.54-1.68 (br, 1H), 1.41 (s, 9H), 1.08-1.30 (m, 4H); $^{13}$C NMR (75 MHz, CDCl$_3$): 155.2, 148.2, 148.1, 140.6, 136.3, 134.1, 128.7, 127.1, 123.4, 79.0, 55.4, 50.6, 49.4, 31.9, 28.3; MS (EI) calcd for C$_{23}$H$_{31}$N$_3$O$_2$ (M$^+$) 381; found 381.

Preparation of [4-(4-pyridin-4-yl-benzylamino)-cyclohexyl]-carbamic acid tert-butyl ester (18c): Product 18c (365 mg) was obtained in 96% yield; $^1$H NMR (300 MHz, CDCl$_3$) 8.62 (d, J=5.4 Hz, 2H), 7.31-7.60 (m, 6H), 4.30-4.40 (br, 1H), 3.84 (s, 2H), 3.34-3.46 (br, 1H), 2.40-2.58 (m, 1H), 1.92-2.08 (m, 4H), 1.50-1.64 (br, 1H), 1.42 (s, 9H), 1.03-1.35 (m, 4H); $^{13}$C NMR (75 MHz, CDCl$_3$): δ 155.2, 150.1, 148.0, 141.7, 136.7, 128.8, 127.0, 121.5, 79.1, 58.3, 55.5, 50.7, 49.5, 31.9, 28.4; MS (EI) calcd for C$_{23}$H$_{31}$N$_3$O$_2$ (M$^+$) 381; found 381.

Preparation of [4-(3-pyridin-4-yl-benzylamino)-phenyl]-carbamic acid tert-butyl ester (18d): Product 18d (348 mg) was obtained in 93% yield; $^1$H-NMR (300 MHz, CDCl$_3$): 8.63 (d, J=6.0 Hz, 2H), 7.66 (s, 1H), 7.44-7.53 (m, 3H), 7.44 (d, J=4.8 Hz, 2H), 7.19 (d, J=7.5 Hz, 2H), 6.59 (d, J=8.7 Hz, 2H), 4.37 (s, 2H), 1.49 (s, 9H); $^{13}$C NMR (75 MHz, CDCl$_3$): 153.4, 150.0, 148.0, 144.1, 140.6, 138.2, 129.2, 129.0, 128.0, 125.8, 125.6, 121.5, 121.0, 113.2, 79.7, 48.3, 28.2; MS (EI) calcd for C$_{11}$H$_{25}$N$_3$O$_2$ (M$^+$) 375; found 375.

Preparation of [4-(3-pyridin-3-yl-benzylamino)-phenyl]-carbamic acid tert-butyl ester (18e): Product 18e (356 mg) was obtained in 95% yield; $^1$H-NMR (300 MHz, CDCl$_3$): 8.84 (d, J=1.5 Hz, 1H), 8.60 (dd, J$_1$=4.8 Hz, J$_2$=1.5 Hz, 1H), 7.85-7.89 (m, 1H), 7.48 (s, 1H), 7.42-7.47 (m, 4H), 7.17 (d, J=8.7 Hz, 2H), 6.61 (d, J=8.7 Hz, 2H), 6.30-6.42 (br, 1H), 4.22 (s, 2H), 4.39-4.41 (br, 1H), 1.42 (s, 9H); $^{13}$C NMR (75 MHz, CDCl$_3$): 153.4, 148.3, 148.2, 144.2, 140.5, 137.9, 136.3, 134.3, 129.2, 129.1, 127.1, 126.0, 125.9, 125.8, 123.4, 121.0, 113.2, 113.1, 79.6, 67.8, 48.4, 28.3, 25.5; MS (EI) calcd for C$_{23}$H$_{25}$N$_3$O$_2$ (M$^+$) 375; found 375.

Preparation of [4-(4-pyridin-3-yl-benzylamino)-phenyl]-carbamic acid tert-butyl ester (18f): Product 18f (348 mg) was obtained in 93% yield; $^1$H-NMR (300 MHz, CDCl$_3$): 8.86-8.87 (m, 1H), 8.60-8.63 (m, 1H), 7.86-7.91 (m, 1H), 7.40-7.60 (m, 5H), 7.30-7.40 (m, 2H), 7.18 (d, J=13.2 Hz, 2H), 6.62 (d, J=13.2 Hz, 2H), 6.31-6.42 (br, 1H), 4.40 (s, 2h), 3.95-4.10 (br, 1H), 1.52 (s, 9H); $^{13}$C NMR (75 MHz, CDCl$_3$) 153.4, 148.3, 148.1, 144.3, 139.6, 136.5, 136.3, 134.2, 128.9, 128.0, 127.2, 123.5, 121.2, 113.2, 79.5, 48.1, 28.3; MS (EI) calcd for C$_{23}$H$_{25}$N$_3$O$_2$ (M$^+$) 375; found 375.

Preparation of [4-(4-pyridin-3-yl-benzylamino)-phenyl]-carbamic acid tert-butyl ester (18g): Product 18 g (352 mg) was obtained in 94% yield; $^1$H-NMR (300 MHz, CDCl$_3$) 8.62-8.65 (m, 2H), 7.43-7.61 (m, 6H), 7.13 (d, J=13.5 Hz, 2H), 6.57 (d, J=13.2 Hz, 2H), 6.13-6.27 (br, 1H), 3.92-4.02 (br, 1H), 1.48 (s, 9H); $^{13}$C NMR (75 MHz, CDCl$_3$): 153.4, 150.3, 148.0, 144.2, 140.7, 137.0, 128.9, 128.0, 127.2, 121.5, 121.2, 113.3, 80.0, 48.2, 28.4; MS (EI) calcd for C$_{23}$H$_{25}$N$_3$O$_2$ (M$^+$) 375; found 375.

General procedure for preparation of 19a-19h: To a solution of substrate 18a-18g (1.0 mmol) and Et$_3$N (280 µL, 2.0 mmol) in CH$_2$Cl$_2$ (10 mL) were added the corresponding acyl chloride 12, 12a-12b (1.1 mmol, prepared by reaction of the individual acid with SOCl$_2$), and the mixture was stirred at room temperature for 0.5 h. The reaction was worked up by removal of solvent, and the residue was purified by a flash chromatography on silica gel (acetone/PE=5/1) to give the products 19a-19h.

Preparation of {4-[(3-chloro-benzo[b]thiophene-2-carbonyl)-(4-pyridin-3-yl-benzyl)-amino]-cyclohexyl}-carbamic acid tert-butyl ester (19a): Product 19a (552 mg) was obtained in 96% yield; $^1$H-NMR (300 MHz, CDCl$_3$): 8.83 (d, J=1.8 Hz, 1H), 8.57 (dd, J$_1$=7.2 Hz, J$_2$=4 Hz, 1H), 8.04-8.10 (m, 1H), 7.95-8.00 (m, 1H), 7.84-7.87 (m, 1H), 7.50-7.60 (m, 4H), 7.40-7.50 (m, 3H), 6.16 (d, J=11.4 Hz, 1H), 4.79 (s 2H), 3.75-3.86 (br, 1H), 3.14-3.21 (m, 1H), 1.71-1.81 (m, 6H), 1.33 (s, 9H), 1.08-1.30 (m, 2H); $^{13}$C NMR (50 MHz, CDCl$_3$): 163.5, 155.0, 148.4, 148.1, 138.9, 138.0, 137.1, 135.5, 134.3, 129.2, 126.5, 125.4, 123.4, 122.6, 122.3, 118.9, 79.1, 58.2, 48.7, 44.5, 32.1, 30.3, 28.2; HRMS (EI) calcd for C$_{32}$H$_{34}$ClN$_3$O$_3$S [M$^+$] 575.2009; found 575.2018.

Preparation of {4-[(benzo[b]thiophene-2-carbonyl)-(4-pyridin-3-yl-benzyl)-amino]-cyclohexyl}-carbamic acid tert-butyl ester (19b): Product 19b (503 mg) was obtained in 93% yield; $^1$H-NMR (300 MHz, CDCl$_3$): 8.86 (d, J=3.0 Hz, 1H), 8.58 (dd, J$_1$=6.6 Hz, J$_2$=2.1 Hz, 1H), 7.60-7.86 (m, 3H), 7.32-7.60 (m, 8H), 4.81 (s, 2H), 4.35-4.57 (br, 1H), 4.20-4.30 (br, 1H), 3.20-3.41 (br, 1H), 2.00-2.04 (m, 2H), 1.86-1.89 (m, 2H), 1.50-1.80 (m, 2H), 1.40 (s, 9H), 1.13-1.41 (m, 2H); $^{13}$C NMR (75 MHz, CDCl$_3$): 165.5, 155.1, 148.4, 148.1, 140.1, 138.7, 138.6, 136.7, 134.1, 127.5, 127.3, 125.7, 124.7, 124.6, 123.5, 122.2, 79.2, 57.2, 48.6, 32.3, 29.8, 28.3; HRMS (EI) calcd for C$_{32}$H$_{35}$N$_3$O$_3$S 541.2399, Found 541.2398.

Preparation of {4-[(benzo[b]thiophene-2-carbonyl)-(3-pyridin-3-yl-benzyl)-amino]-cyclohexyl}-carbamic acid tert-butyl ester (19c): Product 19c (508 mg) was obtained in 93% yield; $^1$H-NMR (300 MHz, CDCl$_3$): 8.83 (s, 1H), 8.60 (d, J=3.0 Hz, 1H), 7.75-7.86 (m, 3H), 7.34-7.50 (m, 8H), 4.83 (s, 2H), 4.38-4.52 (br, 1H), 4.22-4.38 (br, 1H), 3.20-3.41 (br, 1H), 2.00-2.04 (m, 2H), 1.68-1.89 (m, 2H), 1.54-1.64 (m, 2H), 1.41 (s, 9H), 1.16-1.35 (m, 2H); $^{13}$C NMR (75 MHz, CDCl$_3$): δ 165.5, 155.0, 148.4, 148.3, 148.1, 140.0, 138.6, 137.4, 136.3, 134.4, 129.3, 127.4, 127.3, 126.0, 125.4, 125.1, 124.6, 123.5, 122.2, 79.2, 58.0, 48.6, 32.3, 29.6, 29.5, 28.3; HRMS (EI) calcd for $C_{32}H_{35}N_3O_3S$ [M+] 541.399; found 541.2392.

Preparation of {4-[(benzo[b]thiophene-2-carbonyl)-(4-pyridin-4-yl-benzyl)-amino]-cyclohexyl}-carbamic acid tert-butyl ester (19d): Product 19d (503 mg) was obtained in 93% yield; $^1$H-NMR (300 MHz, CDCl$_3$): 8.64-8.85 (br, 2H), 7.70-7.87 (m, 2H), 7.30-7.68 (m, 9H), 4.85 (s, 2H), 4.26-4.41 (br, 1H), 3.30-3.51 (br, 1H), 2.03-2.07 (m, 2H), 1.88-1.92 (m, 2H), 1.56-1.81 (m, 2H), 1.44 (s, 9H), 1.15-1.30 (m, 2H); $^{13}$C NMR (75 MHz, CDCl$_3$): 163.5, 155.0, 150.1, 147.7, 139.3, 137.1, 136.7, 135.5, 130.0, 127.6, 127.0, 125.4, 122.6, 122.4, 121.4, 119.0, 79.1, 58.7, 48.5, 44.8, 32.0, 29.1, 28.2; HRMS (EI) calcd for $C_{32}H_{35}N_3O_3S$ [M+] 541.2399; found 541.2398.

Synthesis of {4-[(chloro-benzo[b]thiophene-2-carbonyl)-(3-pyridin-4-yl-benzyl)-amino]-phenyl}-carbamic acid tert-butyl ester (19e): Product 19e (546 mg) was obtained in 96% yield; $^1$H-NMR (200 MHz, CDCl$_3$): 8.61-8.80 (br, 2H), 7.63-7.70 (m, 6H), 7.33-7.56 (m, 4H), 6.97-7.24 (m, 4H), 5.16 (s, 2H), 1.42 (s, 9H); $^{13}$C NMR (50 MHz, CDCl$_3$): 163.0, 152.4, 149.2, 148.7, 138.2, 137.7, 137.6, 135.3, 130.3, 129.6, 129.4, 128.1, 127.2, 126.4, 126.2, 125.6, 125.0, 122.5, 122.1, 120.6, 119.7, 80.5, 53.7, 28.0; HRMS (EI) calcd for $C_{32}H_{28}ClN_3O_3S$ [M+] 569.1539; found 569.1532.

Preparation of {4-[(3-chloro-benzo[b]thiophene-2-carbonyl)-(4-pyridin-3-yl-benzyl)-amino]-phenyl}-carbamic acid tert-butyl ester (19f): Product 19f (540 mg) was obtained in 95% yield; $^1$H-NMR (200 MHz, CDCl$_3$): 8.83 (s, 1H), 8.55 (d, J=3.6 Hz, 1H), 7.83 (m, 1H), 7.21-7.72 (m, 121H), 6.99 (d, J=8.6 Hz, 2H), 5.13 (s, 2H), 1.41 (s, 9H); $^{13}$C NMR (50 MHz, CDCl$_3$): 162.9, 152.5, 147.9, 147.6, 138.3, 137.5, 136.6, 136.5, 136.0, 135.3, 135.2, 134.3, 130.4, 129.2, 128.0, 127.0, 126.2, 124.9, 123.5, 122.4, 122.3, 120.5, 118.3, 80.3, 53.4, 28.0; HRMS (EI) calcd for $C_{32}H_{28}ClN_3O_3S$ [M+] 569.1539; found 569.1523.

Preparation of {4-[(benzo[b]thiophene-2-carbonyl)-(4-pyridin-4-yl-benzyl)-amino]-phenyl}-carbamic acid tert-butyl ester (19g): Product 19g (518 mg) was obtained in 97% yield; $^1$H-NMR (200 MHz, CDCl$_3$) 8.60-8.79 (br, 2H), 7.30-7.78 (m, 10H), 7.18 (d, J=5.8 Hz, 2H), 6.99 (d, J=5.5 Hz, 2H), 6.49 (s, 1H), 5.14 (s, 2H), 1.44 (s, 9H); $^{13}$C NMR (50 MHz, CDCl$_3$): 163.0, 152.4, 150.0, 149.9, 147.9, 138.2, 137.7, 137.6, 137.1, 135.5, 135.3, 130.4, 129.4, 128.7, 128.3, 128.1, 127.6, 127.1, 126.4, 125.5, 125.0, 123.8, 122.7, 122.5, 122.4, 1215, 120.7, 118.3, 80.6, 53.5, 258.1; HRMS (EI) calcd for $C_{32}H_{29}N_3O_3S$ [M+] 535.1929; found 535.1933.

Preparation of {4-[(benzofuran-2-carbonyl)-(4-pyridin-4-yl-benzyl)-amino]-phenyl}-carbamic acid tert-butyl ester (19h): Product 19h (493 mg) was obtained in 95% yield; $^1$H-NMR (300 MHz. CDCl$_3$): 8.63 (d, J=5.7 Hz, 2H), 7.05-7.56 (m, 12H), 7.00-7.05 (m, 2H), 6.15 (s, 1H), 5.10 (s, 2H), 1.49 (s, 9H); $^{13}$C NMR (75 MHz, CDCl$_3$): 159.9, 154.3, 152.6, 150.0, 147.8, 147.4, 138.9, 137.8, 137.0, 136.2, 129.7, 128.8, 126.9, 126.8, 126.6, 123.2, 122.3, 121.4, 118.8, 112.5, 111.8, 80.6, 54.0, 28.2; HRMS (EI) calcd for $C_{32}H_{29}N_3O_3S$ 535.1929, found 535.1933.

General procedure for preparation of 21a-21e: To a solution of compound 19x (x=a-h, 0.1 mmol) in DMF (6.0 mL) was added water (2 µL), followed by addition of NaH (~60 mg, 60% suspension in mineral oil), and the mixture was stirred at 0° C. for 1 h. To this solution was added organohalides at 0° C., and the mixture was stirred at room temperature for 5 h. The reaction was worked up by addition of a saturated solution of NaH CO$_3$ (10 mL), the mixture was first extracted with Et$_2$O (3×20 mL), and the combined extract was then dried over anhydrous Na$_2$SO$_4$. The solvent was removed under vacuum and the residue was purified by semi-preparative HPLC (96X250 XDB C18 column (100% CH$_3$CN, 3 mL/min) to give the alkylated product 20x, which was dissolved in CH$_2$Cl$_2$ (1.0 mL). Trifluoroacetic acid (1.0 mL) was added at 0° C., and the mixture was stirred at room temperature for 4 h. The reaction was worked up by addition of a saturated solution of Na$_2$CO$_3$ (2 mL), and the mixture was extracted with CH$_2$Cl$_2$ (3×5 mL), and the combined organic layers were dried over anhydrous Na$_2$SO$_4$. The solvent was removed under vacuum, and the residue was purified by a flash chromatography on silica gel (CH$_2$Cl$_2$/acetone/TEA=40/10/1) to give compound 21x.

Preparation of 3-chloro-benzo[b]thiophene-2-carboxylic acid (4-allylamino-cyclohexyl)-(3-pyridin-4-yl-benzyl)-amide (also named, N-(trans-4-(allylamino)cyclohexyl)-3-chloro-N-(3-(pyridin-4-yl)benzyl)benzo[b]thiophene-2-carboxamide 21a): Compound 19 (57 mg, 0.10 mmol) was treated with 3-bromoprop-1-ene (25 uL) (25 uL) according to the general protocol to afford 20a (58 mg) in 94% yield; $^1$H NMR (300 MHz, d6-DMSO, T=353K): 8.64 (d, J=4.5 Hz, 2H), 8.08 (d, J=7.5 Hz, 1H), 7.87 (d, J=7.5 Hz, 1H), 7.40-7.70 (m, 8H), 5.64-5.73 (m, 1H), 4.96-5.05 (m, 2H), 4.80 (s, 2H), 3.80-3.92 (br, 1H), 3.60-3.65 (m, 2H), 3.48-3.56 (br, 1H), 1.70-1.86 (br, 4H) 1.40-1.70 (b, 4H), 1.29 (s, 9H); $^{13}$C NMR (75 MHz, CDCl$_3$): 163.6, 155.1, 150.2, 147.9, 139.2, 138.5, 137.3, 135.9, 135.7, 130.4, 129.2, 127.6, 126.4, 125.8, 125.6, 125.4, 122.7, 122.6, 122.5, 122.4, 121.5, 119.0, 115.2, 79.5, 54.4, 45.7, 36.2, 29.7, 28.3; HRMS (ESI) calcd for $C_{35}H_{39}ClN_3O_3S$ (M+H+) 616.2395; found 616.2388.

Compound 20a (58 mg) was treated with TFA as described in the general procedure to give product 21a (45 mg) in 94% yield; $^1$H-NMR (300 MHz, d6-DMSO, T=353K): 8.65 (d, J=6.0 Hz, 2H), 8.08 (d, J=7.2 Hz, 1H), 7.86-7.90 (m, 1H), 7.40-7.80 (m, 8H), 5.74-5.83 (m, 1H), 5.11 (d, J=17.4 Hz, 1H), 4.99 (d, J=10.2 Hz, 1H), 4.79 (s, 2H), 3.74-3.90 (br, 1H), 3.07-3.14 (m, 2H), 2.35-2.50 (m, 2H), 1.82-1.94 (m, 2H), 1.62-1.81 (m, 4H), 0.89-0.96 (m, 2H); $^{13}$C NMR (75 MHz, CDCl$_3$): 163.5, 150.1, 147.9, 139.1, 138.3, 137.1, 136.4, 135.5, 129.1, 127.5, 126.4, 125.6, 125.55, 122.5, 122.3, 121.4, 118.8, 115.8, 58.8, 54.8, 49.2, 45.3, 32.0, 30.0; HRMS (ESI) calcd for $C_{30}H_{31}ClN_3OS$(M+H+) 516.1871, found 516.1861.

Preparation of 3-chloro-benzo[b]thiophene-2-carboxylic acid (4-propylamino-cyclohexyl)-(3-pyridin-4-yl-benzyl)-amide (also named, 3-chloro-N-(trans-4-(propylamino)cyclohexyl)-N-(3-(pyridin-4-yl)benzyl)benzo[b]thiophene-2-carboxamide 21b): Compound 19 (57 mg, 0.10 mmol) was treated with 1-iodopropane (25 uL) according to the general protocol to afford 20b (59 mg) in 96% yield; $^1$H NMR (300 MHz, d6-DMSO, T=353K): 8.64 (dd, $J_1$=4.5 Hz, $J_2$=1.5 Hz, 2H), 8.07 (d, J=7.5 Hz, 1H), 7.85-7.88 (m, 1H), 7.48-7.61 (m, 8H), 4.80 (s, 2H), 3.80-3.93 (br, 1H), 3.30-3.50 (br, 1H), 2.84-2.96 (m, 2H), 1.70-1.86 (m, 4H), 1.51-1.70 (m, 4H), 1.27-1.42 (m, 2H), 1.27 (s, 9H), 0.72-0.77 (m, 3H); $^{13}$C NMR (75 MHz, CDCl$_3$, T=328K): 163.6, 155.3, 150.2, 139.3, 139.2, 137.3, 135.7, 130.6, 129.2, 127.6, 126.4, 125.6, 125.4, 122.7, 122.5, 121.5, 119.0, 79.2, 54.6, 54.5, 45.5, 30.9, 28.4, 23.6, 11.2; HRMS (ESI) calcd for $C_{35}H_{41}ClN_3O_3S$ (M+H+) 618.2551; found 618.2503.

Compound 20b (59 mg) was treated with TFA as described in the general procedure to give product 21b (46 mg) in 94% yield; $^1$H-NMR (300 MHz, d6-DMSO, T=353K): δ 8.65 (dd, $J_1$=4.5 Hz, $J_2$=1.2 Hz, 2H), 8.08 (d, J=7.5 Hz, 1H), 7.87 (m, 1H), 7.44-7.69 (m, 8H), 4.79 (s, 2H), 3.74-3.90 (br, 1H), 2.48-2.57 (m, 2H), 1.88-1.95 (m, 2H), 1.67-1.77 (m, 4H), 1.34-1.43 (m, 2H), 0.91-1.10 (br, 2H), 0.83 (t, J=4.5 Hz, 3H); $^{13}$C NMR (75 MHz, CDCl$_3$, T=328K): 163.7, 150.2, 147.9, 139.1, 138.5, 137.2, 135.6, 129.3, 127.6, 126.5, 125.6, 125.5, 122.6, 122.5, 121.5, 119.1, 58.4, 55.6, 48.0, 45.3, 30.7, 29.6, 21.9, 11.4; HRMS (ESI) calcd for $C_{30}H_{33}ClN_3OS$ (M+H$^+$) 518.2027; found 518.1992.

Preparation of benzofuran-2-carboxylic acid (4-methylamino-phenyl)-(3-pyridin-4-yl-benzyl)-amide (21c): Compound 19h (52 mg, 0.1 mmol) was treated with MeI (15 uL) according to the general protocol to afford 20c (51 mg) in 94% yield; $^1$H-NMR (300 MHz, CDCl$_3$, T=353K): δ 8.65 (d, J=8.4 Hz, 2H), 7.06-7.61 (m, 14H), 6.30 (s, 1H), 5.14 (s, 2H), 3.28 (s, 3H), 1.46 (s, 9H); $^{13}$C NMR (75 MHz, CDCl$_3$): δ 159.9, 154.4, 154.3, 150.3, 150.2, 147.7, 147.6, 143.7, 138.8, 137.8, 137.2, 129.6, 128.2, 127.1, 127.0, 126.8, 126.7, 126.1, 123.3, 122.3, 121.4, 112.6, 111.8, 80.7, 53.9, 37.1, 28.2; HRMS (ESI) calcd for $C_{33}H_{32}N_3O_4$ (M+H$^+$) 534.2387; found 534.2376.

Compound 20c (51 mg) was treated with TFA as described in the general procedure to give 21c (36 mg) in 90% yield; $^1$H-NMR (300 MHz, CDCl$_3$): δ 8.66 (d, J=4.5 Hz, 2H), 7.15-7.60 (m, 10H), 6.90 (d, J=8.7 Hz, 2H), 6.54-6.57 (m, 2H), 6.00 (s, 1H), 5.10 (s, 2H), 3.95-4.05 (br, 1H), 2.86 (s, 3H); $^{13}$C NMR (75 MHz, CDCl$_3$): δ 160.1, 154.4, 150.2, 149.2, 147.9, 147.8, 138.3, 137.1, 131.3, 129.9, 129.2, 127.2, 126.9, 126.5, 123.1, 122.4, 121.5, 112.7, 112.2, 111.9, 54.2, 30.6; HRMS (ESI) calcd for $C_{28}H_{24}N_3O_2$ (M+H$^+$) 434.1863; found 434.1854.

Preparation of benzofuran-2-carboxylic acid (4-ethylamino-phenyl)-(3-pyridin-4-yl-benzyl)-amide (21d): Compound 19h (52 mg, 0.1 mmol) was treated with iodoethane (25 uL) according to the general protocol to afford 20d (51 mg) in 95% yield; $^1$H-NMR (300 MHz, CDCl$_3$): 8.66 (d, J=4.8 Hz, 2H), 7.08-7.60 (m, 14H), 6.34 (s, 1H), 5.16 (s, 2H), 3.70 (q, J=6.9 Hz, 2H), 1.44 (s, 9H), 1.16 (t, J=6.9 Hz, 3H); $^{13}$C NMR (75 MHz, CDCl$_3$): 159.9, 154.4, 154.1, 150.2, 147.7, 142.3, 139.5, 137.8, 137.3, 129.6, 128.4, 127.8, 127.0, 126.7, 123.3, 122.2, 121.5, 112.6, 111.8, 80.4, 53.9, 44.6, 28.3, 13.8. HRMS (EI) calcd for $C_{34}H_{34}N_3O_4$ (M+H$^+$) 548.2544; found 548.2534.

Compound 20d (51 mg) was treated with TFA as described in the general procedure to give 21d (39 mg) in 93% yield; $^1$H-NMR (300 MHz, CDCl$_3$): δ 8.72 (d, J=3.6 Hz, 2H), 7.68 (d, J=6.0 Hz, 2H), 7.61 (d, J=8.1 Hz, 2H), 7.50 (d, J=8.1 Hz, 2H), 7.43 (d, J=5.7 Hz, 2H), 7.28-7.33 (m, 1H), 7.12-7.19 (m, 1H), 6.88 (dd, J$_1$=6.6 Hz, J$_2$=1.8 Hz, 2H), 6.54 (dd, J$_1$=6.6 Hz, J$_2$=1.8 Hz, 2H), 6.17 (s, 1H), 5.09 (s, 2H), 3.16 (q, J=7.2 Hz, 2H), 1.26 (t, J=7.2 Hz, 3H); $^{13}$C NMR (75 MHz, CDCl$_3$): δ 160.3, 154.5, 151.3, 148.4, 148.0, 147.0, 139.8, 135.8, 131.5, 130.1, 129.2, 127.2, 126.5, 123.1, 122.3, 113.1, 112.3, 111.9, 54.3, 38.5, 14.6; HRMS (EI) calcd for $C_{29}H_{26}N_3O_2$ (M+H$^+$) 448.2019; found 448.2011.

Preparation of benzofuran-2-carboxylic acid (4-butylamino-phenyl)-(3-pyridin-4-yl-benzyl)-amide (21e): Compound 19h (52 mg, 0.11 mmol) was treated with 1-Iodobutane (40 uL) according to the general protocol to give 20e (55 mg, 95% yield); $^1$H NMR (400 MHz, CDCl$_3$): δ 8.64 (d, J$_1$=4.2 Hz, 2H), 7.58 (d, J$_2$=8.0 Hz, 2H), 7.45-7.49 (m, 4H), 7.41 (d, J=7.8 Hz, 1H), 7.36 (s, 1H), 7.30 (d, J=12.8 Hz, 1H), 7.19 (dd, J$_1$=8.4 Hz, J$_2$=6.8 Hz, 3H), 7.09 (d, J=8.4 Hz, 2H), 6.35 (s, 1H), 5.15 (s, 2H), 3.65 (t, J=7.2 Hz, 2H), 1.4-1.53 (m, 2H), 1.44 (s, 9H), 1.29-1.34 (m, 2H), 0.86-0.93 (t, J=7.2 Hz, 3H); $^{13}$C NMR (100 MHz, CDCl$_3$): δ 159.8, 154.4, 154.2, 150.2, 147.7, 142.5, 139.4, 137.8, 137.2, 129.6, 128.3, 127.8, 127.0, 126.8, 126.7, 123.3, 122.2, 121.4, 112.6, 111.8, 80.3, 53.9, 49.4, 30.5, 28.2, 19.8, 13.7; HRMS (EI) calcd for $C_{36}H_3N_3O_4$ (M+H$^+$) 576.2857; found 576.2856.

Compound 20e (55 mg) was treated with TFA as described in the general procedure to give 21e (42 mg) in 94% yield; $^1$H NMR (300 MHz, CDCl$_3$): δ 8.65 (dd, J$_1$=4.5 Hz, J$_2$=1.5 Hz, 2H), 7.10-7.60 (m, 10H), 6.88 (d, J=8.7 Hz, 2H), 6.55 (d, J=8.7 Hz, 2H), 6.01 (s, 1H), 5.09 (s, 2H), 3.80-3.94 (br, 2H), 3.01-3.18 (br, 2H), 1.63 (t, J=7.2 Hz, 2H), 1.40-1.48 (m, 2H), 0.97 (t, J=7.2 Hz, 3H); $^{13}$C NMR (75 MHz, CDCl$_3$): 160.1, 154.3, 150.2, 148.4, 147.7, 138.3, 137.0, 131.0, 129.8, 128.2, 127.1, 126.8, 126.5, 123.1, 122.3, 121.4, 113.0, 112.9, 112.2, 111.9, 54.2, 43.5, 31.4, 20.2, 13.9; HRMS (ESI) Calculated for $C_{31}H_{30}N_3O_2$(M+H$^+$) 476.2333, Found 476.2319.

Example II

Potent Antagonists of Smoothened for Inhibiting Hedgehog Signaling

The seven-pass transmembrane protein Smoothened (Smo) is an essential component of the Hedgehog (Hh) signaling pathway that is critically involved in normal animal development as well as pathological malignancies. In accordance with certain aspects of the technology, using Gli1-dependent GFP and other transgenic zebrafish embryonic assays, potent new small molecule inhibitors of Hh signaling were identified and characterized.

A Gli-GFP transgenic zebrafish model that allows in vivo detection of Hh activity in whole living embryos was developed. Since genetic Hh deficient zebrafish embryos have defined phenotypes, they can be used to characterize efficiency and specificity of the inhibitors. For instance, treatment of zebrafish embryos with cyclopamine will induce characteristic U-shape somites, shorter intersegmental blood vessels and fewer beta cells of pancreas that are observed in Smo mutations of zebrafish.

SAG, an Hh pathway agonist that has binding affinity to Smo protein in a manner antagonizing cyclopamine action, was used as a control compound.

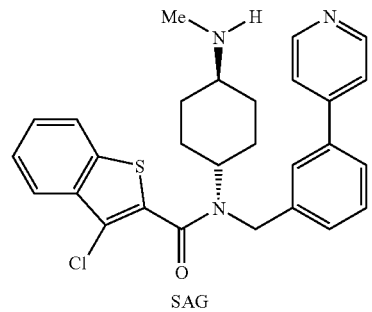

SAG

Here, at least two compounds were identified that demonstrate a high potency and specificity of inhibiting Hh through binding to Smo.

Experimental Procedures

Generation of Gli:GFP transgenic zebrafish. A DNA fragment containing 8× Gli binding site with a minimal promoter was generated by PCR from Gli-dependent firefly luciferase plasmids (Sasaki H, Hui C, Nakafukui M, Kondoh H, "A binding site for Gli proteins is essential for HNF-3beta floor plate enhancer activity in transgenics and can respond to Shh in vitro" Development 1997; 124:1313-22; incorporated herein by reference) using primer 8gli-f (CGAGCTAGCG-GATCCCCGGGAACAGATTC (SEQ ID NO: 1)) and 8gli-r (GCGACGCGTTTTACCAACAGTACCGG (SEQ ID NO: 2)). The PCR product digested with Nhe1 and Mlu1 was ligated to GFP and used to generate transgenic zebrafish by microinjection. 8 founder lines expressing GFP were identified that reflect the pattern of Hh-signaling activity in developing embryos. Four lines exhibiting stronger expression throughout development were maintained and used in this study.

Screening methods. Embryos (3 per well) were distributed to 96-well-plates in Holfreter's buffer containing approximately 80 μM of individual compounds from the library and incubated at 28.5° C. Phenotypes were observed at 36 hpf and 48 hpf separately. After the initial screen several top candidate compounds with highest activity were analyzed further at different concentrations ranging from 10 μM to 80 μM.

Image acquisition and analysis. GFP-positive embryos or larvae were viewed under an Axioimager Z1 fluorescence microscope (Zeiss), equipped with 5, 10 and 20× lenses, and filter set 10 for detection of GFP (excitation: 450-490 nm barrier: 510 nm, emission: 515-565 nm).

Quantitative Real-time PCR. The larvae were exposed to different concentrations of small molecules from 2 hpf. Total RNA was extracted from the embryos at 36 hpf using the Trizol kit (Ambion, Austin, Tex.) according to the manufacturer's instructions. Three groups per treatment, each composed of 20 embryos, were assayed using SYBRGreen qPCR kit by real-time PCR (ABI Prism 7700 Sequence Detector System).

Primer sequences used were as follows:

```
zgli1-f      GGGGAACATCTACAGTCATC    (SEQ ID NO: 3)

zgli1-r      GTGGCAGTTCGTCTCATAAA    (SEQ ID NO: 4)

zptc1-f      TGATTGTGACTCCTTTGG      (SEQ ID NO: 5)

zptc1-r      TCCTTATTAGGGGCACTG      (SEQ ID NO: 6)

zbactin1-f   CTATGAGCTGCCTGACGG      (SEQ ID NO: 7)

zbactin1-R   TGGTGGAAGGAGCAAGAG      (SEQ ID NO: 8)
```

Compound activities in Shh-LIGHT2 cells. Shh-LIGHT2 cells (ATCC CRL-2795), a NIH-3T3 cell line stably incorporating Gli-dependent firefly luciferase and thymidine kinase promoter-driven Renilla luciferase reporters (Taipale J, Chen J K, Cooper M K, Wang B. Mann R K, Milenkovic L. et al. "Effects of oncogenic mutations in Smoothened and Patched can be reversed by cyclopamine" Nature 2000; 406:1005-9; incorporated herein by reference), were cultured to confluency in 96-well plates using DMEM medium containing 10% calf serum, 100 U/mL penicillin, and 100 μg/mL streptomycin. The cells were then treated with various concentrations of the compounds in DMEM containing 0.5% calf serum and a 1:20 dilution of Shh-N-conditioned medium (Chen J. K., Taipale J. Young K. E., Maiti T Beachy P. A., "Small molecule modulation of Smoothened activity" Proc. Natl. Acad. Sci. U.S.A., 2002; 99:14071-6; incorporated herein by reference). The cells were cultured for an additional 30 h under standard conditions. Firefly and Renilla luciferase activities were measured on a Veritas luminometer (Turner Biosystems) using a dual luciferase kit (Promega) according to the manufacturers' protocols.

Smo-binding assay. HEK 293T cells were cultured in DMEM containing 10% fetal bovine serum, 100 U/mL penicillin, and 100 μg/mL streptomycin to 50% confluency in 96-well plates and then transfected with a CMV promoter-driven mouse Smoothened-Myc3 expression construct (100 ng cDNA/well) with Fugene 6 (Roche) according to the manufacturer's protocols. After 12 h the cells were incubated with DMEM containing 0.5% fetal bovine serum, 10 μM Hoechst 33342, 5 nM BODIPY-labeled cyclopamine (Chen J. K., Taipale J, Cooper M. K., Beachy P. A., "Inhibition of Hedgehog signaling by direct binding of cyclopamine to Smoothened" Genes Dev., 2002; 16:2743-8; incorporated herein by reference), and various concentrations of compound 75 for 1 h. The cells were washed two times with PBS buffer and then imaged in DMEM containing 0.5% fetal bovine serum using an ImageXpress 5000A microscopy system (Molecular Devices).

FRET analysis using confocal microscopy. Effect of SAG, compound 21a (SANT74), and compound 21b (SANT75) on mSmo conformational change was tested by FRET in NIH-3T3 cells that were co-transfected with mouse Smo CFP and Smo YFP reporter constructs. The construction of mSmo-CFP$^C$/YFP$^C$, mSmo-CFP$^N$/YFP$^N$, and mSmo-CFP$^{L2}$YFP$^C$ was performed as described in Zhao Y. Tong C, Jiang J., "Hedgehog regulates smoothened activity by inducing a conformational switch" Nature, 2007; 450:252-8; incorporated herein by reference. NIH-3T3 cells were cultured in DMEM containing 10% bovine calf serum and antibiotics PS at 5% $CO_2$ in a humidified incubator. Transfection was carried out using FuGENE6 (Roche). For FRET analysis of cultured cells, CFP- and YFP-tagged constructs were transfected into NIH-3T3 cells. Transfected cells were treated in the presence of compounds with or without Shh-conditioned medium. Cells were washed with PBS, fixed with 4% formaldehyde for 20 min, and mounted on slides in 80% glycerol. Fluorescence signals were acquired with the 100× objective of a Zeiss LSM510 confocal microscope. CFP was excited by 458 nm light and the emission was collected through BP 480-520 nm filter. YFP was excited by 514 nm light and the emission was collected through BP 535-590 nm filter. CFP signal was obtained once before and once after photobleaching YFP using the full power of the 514 nm laser line for 1-2 min at the top half of each cell, leaving the bottom half unbleached that serves as an internal control. The intensity of CFP was analyzed using the Metamorph software (Universal Imaging Corn). Energy transfer efficiency was calculated using the formula: FRET %=(CFPAP−CFPBP/CFPAP)×100. Each data set was based on 10-15 individual cells. In each cell, four to five regions of interest in the photobleached area were selected for analysis.

Results

Gli:GFP Transgenic Zebrafish Generation and Library Screening

In zebrafish, Shh is expressed primarily in notochord during embryogenesis. Stable transgenic zebrafish carrying reporter constructs with 8 Gli binding sites linked to a minimal promoter and GFP were produced. Several lines were obtained in which the transgenic embryos exhibited the strongest GFP expression in the somite tissues immediately adjacent to the midline structure, which has the highest Shh expression. The GFP expression pattern is consistent with the expression of Gli and Ptc1 in zebrafish embryos at the stages analyzed. More importantly, this expression was abolished upon the treatment with cyclopamine. These findings suggested that Gli:GFP expression in these transgenic fish was reflective of the endogenous activity pattern of Shh and is sensitive to Hh signaling level changes induced by chemical inhibitors.

Using these embryos as a tool, a collection of compounds synthesized as described above were tested. Compound 2-d (SANT19) was found to block Gli:GFP expression at approximately 80 µM. Under the same condition, embryos treated with SAG had no effect on Gli:GFP expression. This surprising finding suggests that substituents larger than methyl group possess inhibition activity.

Further screening of compounds led to the identification of SANT74 and SANT75. These two compounds started to show inhibition of Hh signaling at 5 µM and were able to abolish Gli:GFP expression in the zebrafish embryo assays at 20 µM. Compared to SAG, SANT74 and SANT75 have propyl and allyl substitution, which are larger in size than methyl substitution.

Characterization of SANT74 and SANT75 in Zebrafish

Genetic studies have demonstrated that characteristic phenotypes of zebrafish embryos deficient of Hh signaling activity include U-shaped somite, fewer pancreatic insulin positive beta cells and shorter intersegmental blood vessels (ISV). If SANT74 and SANT75 are specific inhibitors of Hh treating, zebrafish embryos should only produce these well-characterized phenotypes. Other developmental abnormality would suggest off-target effects of these compounds. Using these criteria, the specificity of SANT74 and 75 in zebrafish was evaluated. To reveal changes in pancreas and blood vessels, transgenic zebrafish that have beta cells labeled by insulin:GFP and endothelial cells labeled by Flk:GFP were treated with either SANT74 or 75. Treatment with 20 µM SANT74 significantly reduced insulin:GFP cells and ISV. The embryos with defective ISVs also lacked circulation as revealed by microangiographic analysis. The inhibition of angiogenesis by SANT74 is dose dependent and embryos treated with concentration of 20 µM or higher no longer developed any extended ISVs. In zebrafish assay, combining 10 µM of SANT74 and 10 µM of cyclopamine produced an inhibitory effect similar to 20 µM of each compound alone, suggesting additive action on the same protein target of Smo.

As a small molecule, SANT74 offers the temporal control of Hh activity. As a utility of this new inhibitor, timing requirement of Hh for normal somite formation and sprouting of ISV was tested by adding and washing away SANT74 at various developmental stages followed by phenotypic analysis. Before 21 hpf, addition of SANT74 for 4 hours will induce U shape somite formation. When SANT74 was added to the embryos upon fertilization but washed away before 17 hpf the sprouting of ISV could occur normally. To specifically affect ISV without inducing U-shaped somite, SANT74 can be added between 17 and 24 hpf, After 24 hpf adding SANT74 no longer had any effect on the sprouting of ISV. These studies demonstrated that a critical stage for the sprouting of ISV is between 17 and 24 hpf and development of ISV is independent of somite.

Figure 1B:
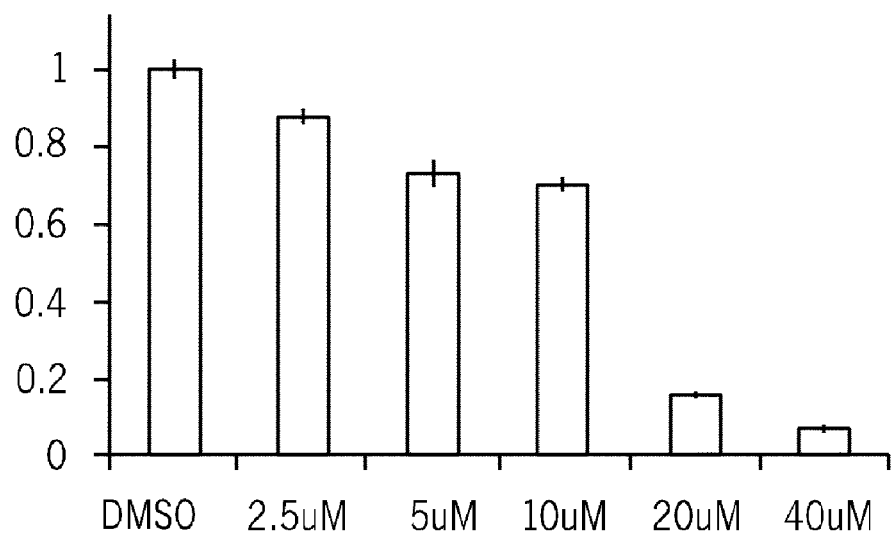

Ptch1 and Gli1 are two target genes of Shh signal pathway and treatment with SANT74 or 75 should inhibit their expression. As measured by real time quantitative PCR. mRNA levels of Ptch1 and Gli1 in zebrafish embryos were reduced by SANT74 or 75 in a dose dependent manner (FIGS. 1A and 1B). Together, these analyses demonstrated that SANT74 and SANT75 are potent and specific inhibitors of Hh in zebrafish.

Characterization of SANT74 and SANT75 in Mammalian Cells

Shh-LIGHT2 cells cultured in Shh-N-conditioned medium were treated with various concentrations of SANT19, SANT74 and SANT75, and luciferase reporter activity was measured as previously reported (Rohatgi R, Scott M. P., "Patching the gaps in Hedgehog signaling", Nat. Cell. Biol., 2007; 9:1005-9; incorporated herein by reference and Chen J. K. et al., Proc. Natl. Acad. Sci. U.S.A., supra). Under these conditions, SANT19, SANT74 and SANT75 had an $IC_{50}$ of 200 nM, 70 nM and 20 nM, respectively, all exhibiting inhibitory potency greater than that of cyclopamine ($IC_{50}$=300 nM). SAG has been shown as an agonist that competes with cyclopamine in binding to Smo protein at its heptahelical bundle (Chen J. K., et al., Genes Dev. supra and Chen J. K. et al., Proc. Natl. Acad. Sci. U.S.A., supra). To determine if the SANT compounds competed with cyclopamine in a similar fashion, Smo-overexpressing HEK 293T cells counterstained with Hoescht 33342 (blue) were incubated with 5 nM BODIPY-cyclopamine (green) and different concentrations of SANT75. SANT75 could effectively abrogate BODIPY-cyclopamine/Smo binding and the competitive concentrations of SANT75 correlated with its $IC_{50}$ in the Shh-LIGHT2 cell assay. These findings confirmed that SANT75 is a competitive inhibitor of cyclopamine that binds to Smo protein in mammalian cells.

Figure 2A:
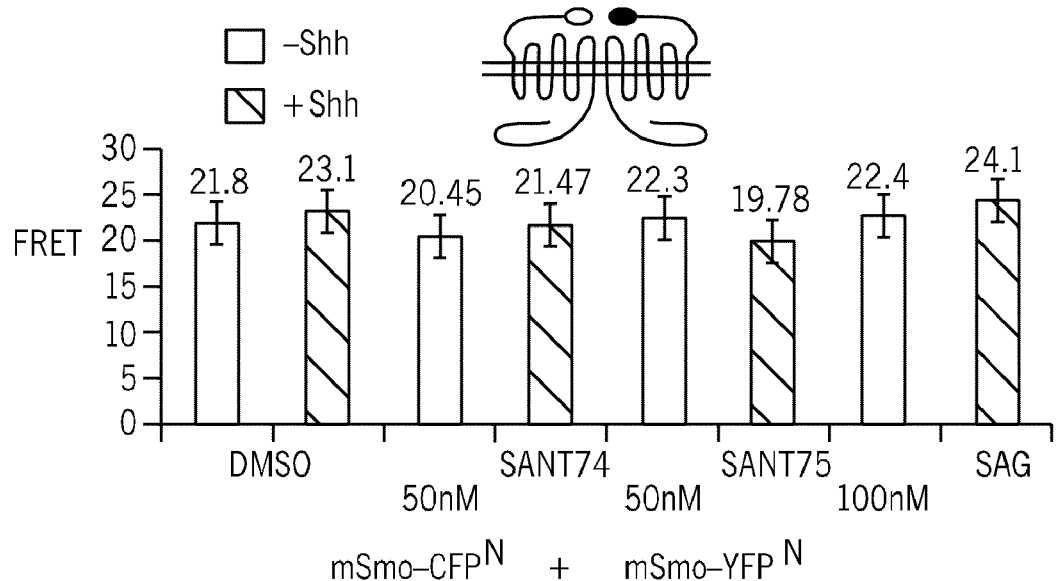
FIG. 2A, Shh independent FRET observed at the extracellular ends is not affected by these compounds.
Figure 2B:
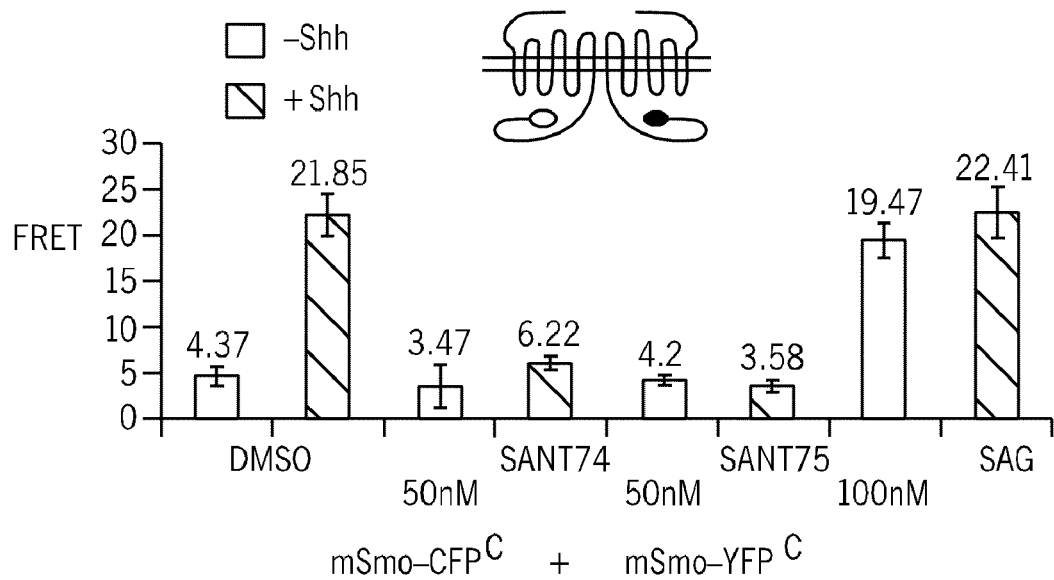
FIG. 2B, Shh induced FRET at the cytoplasmic tails is reduced by SANT 74 and SANT75 but increased by SAG.
Figure 2C:
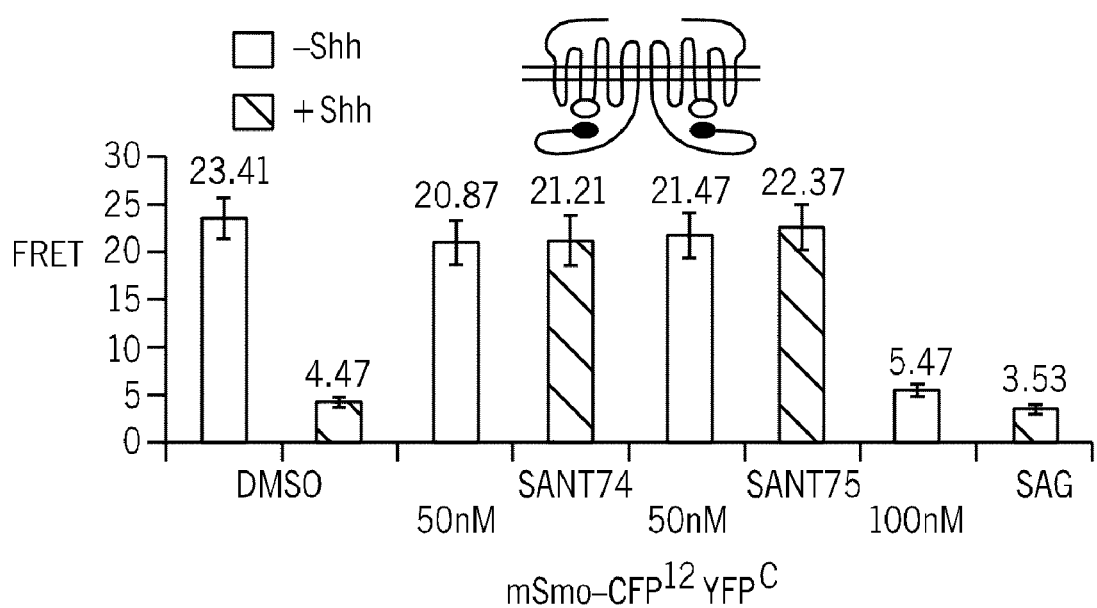
FIG. 2C, Shh inhibited FRET between one cytoplasmic tail and intra-molecular domain is increased by SANT 74 and SANT 75 but reduced by SAG.

A recent study has suggested that Hh regulates Smo activity by inducing a conformational switch resulting in increased proximity of its C-terminal cytoplasmic tails (Zhao Y. et al., Nature, supra). SAG and SANT compounds have very similar structures but modulate Smo activity in opposite directions. These two classes of molecules therefore are likely candidates capable of inducing, active or inactive conformations independent of Hh ligand. To test this, conformation status of Smo was determined by FRET analyses using three pairs of fluorescently tagged Smo: (a) mSmo-$CFP^N$ and mSmOYFP$^N$, which measures the distance between Smo N-termini; (b) mSmo-$CFP^C$ and mSmo-$YFP^C$, which measure the distance between Smo C-termini; and (c) mSmo-$CFP^{L2}YFP^C$, which measures the distance between Smo C-terminus and second intracellular loop (FIG. 2) (see also, Zhao Y et al. Nature, supra). NIHL3T3 cells transfected with mSmo-$CFP^N$ and mSmoYFP$^N$, mSmo-$CFP^C$ and mSmo-$YFP^C$, or mSmo-$CFP^{L2}YFP^C$ were treated with or without Shh and SANT74 (50 nM), or SANT75 (50 nM), or SAG (100 nM). mSmo-$CEP^N$/mSmoYFP$^N$ exhibited high basal FRET that was not affected by either SAG or SANTs (FIG. 2A), consistent with the previous observation that Smo exhibits as a constitutive dimer oligomer (see also, Zhao Y et al., Nature, supra), which is not affected by SAG or SANTs. Shh-induced increase in FRET between mSmo-$CFP^C$ and mSmo-$YFP^C$ ($FRET^C$) was blocked by either SANT74 or SANT75 (FIG. 2B). Similarly, Shh-induced decrease in FRET obtained from mSmo-$CFP^{12}YFP^C$ ($FRET^{L2C}$) was also blocked by SANT74 and SANT75 (FIG. 2C), suggesting that both SANT74 and SANT75 can override Shh-induced Smo conformational change. Thus, SANT appears to lock mSmo in the "closed" inactive conformation. In contrast, SAG induced an increase in $FRET^C$ and decrease in $FRET^{2LC}$ independent of Shh (FIGS. 2B and 2C), suggesting that SAG binding to Smo promotes its "open" active conformation.

Discussion

An effective phenotype-based transgenic zebrafish embryo assay for Hh-signaling pathway inhibitors was developed. This system, using Gli:GFP as a reporter to link activity of a compound to Hh and using other characteristic phenotypes to assess specificity, allows rapid selection of highly potent small molecule inhibitors of Hh. This complements the cell based Hh modulator screen systems that are less effective to eliminate nonspecific compounds. Since the GFP expression in the embryos is specific and reflective of Hh activity it is possible to use this fish line in an automated system to detect simple changes of GFP fluorescence level.

Our screen using zebrafish coupled with mammalian cell assays identified two specific and potent inhibitors, SANT74 and SANT75, of Smo. The $IC_{50}$ values of these two compounds are in the range of a 20-50 nM, which compared to reported small molecule Hh pathway inhibitors, demonstrate high potency for Hh inhibition.

Our tests demonstrated that SAG and SANT74 SANT75 induce opposite conformational change at the cytoplasmic tail but have no effect at the extracellular end of Smo, in a manner corresponding to changes induced by Hh ligand. The structure of SANT75 (or SANT74) only differs from SAG by containing a propyl substitution (or an allyl substitution for SANT74) which are somewhat larger than the methyl group in SAG.

SANT74 and 75 are stronger inhibitors than cyclopamine in mammalian cells and should be useful reagents for studying Hh biology. Cyclopamine is a relatively weak compound, with an $IC_{50}$ of about 300 nM in cultured cells, and has a structure that is less amendable for modification. In addition, cyclopamine is acid-sensitive and therefore is not ideal for oral delivery as a drug candidate. In our studies, SANT74 and 75 are relatively stable and have small structures. Their effects in whole zebrafish embryos assays are specific, showing no obvious off-target toxicity. These observations demonstrate the usefulness of SANT74 and 75 as therapeutic agents.

While certain embodiments have been illustrated and described, it will be understood that changes and modifications can be made therein in accordance with ordinary skill in the art without departing from the present technology in its broader aspects as defined in the following claims.

The invention claimed is:

1. A compound of formula I

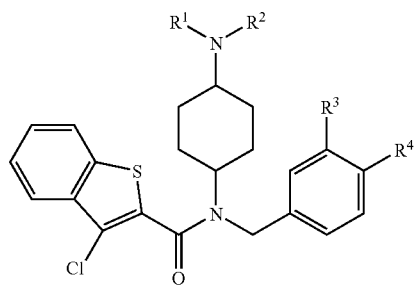

wherein
  $R^1$ is hydrogen or an N-protecting group;
  $R^2$ is a $C_2$-$C_3$ alkyl, haloalkyl or alkenyl group;
  one of $R^3$ and $R^4$ is hydrogen and the other is

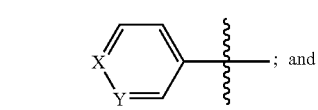

; and one of X and Y is CH and the other is N; or
a stereoisomer thereof, or a pharmaceutically acceptable salt thereof.

2. The compound of claim 1 wherein $R^1$ is hydrogen.

3. The compound of claim 1 of formula IA

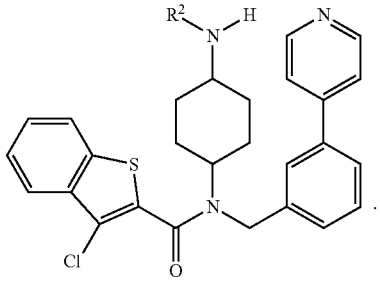

4. The compound of claim 1 of formula I-B

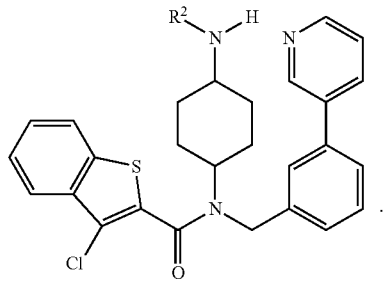

5. The compound of claim 1 of formula I-C

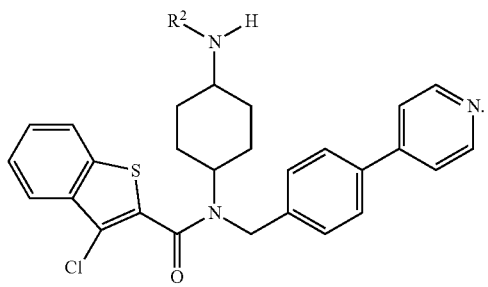

6. The compound of claim 1 of formula I-D

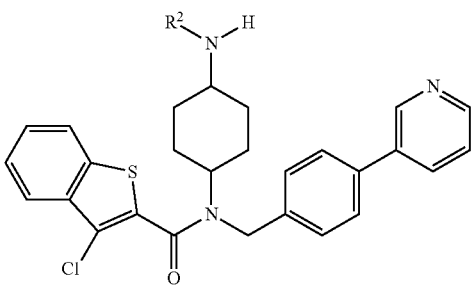

7. The compound of claim 1 of formula I-E

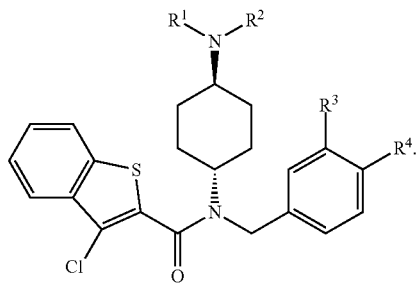

8. The compound of claim 7 of formula I-F

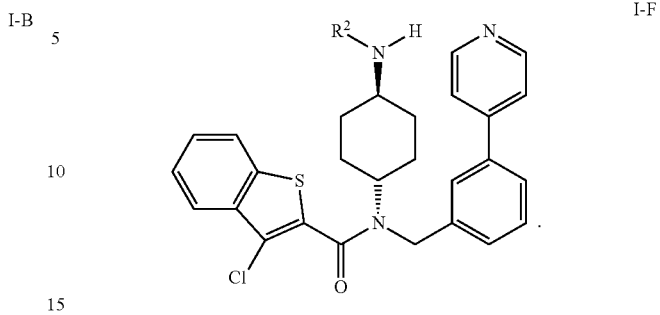

9. The compound of claim 8, wherein $R^2$ is —$CH_2$—$CH_2$—$CH_3$ or —$CH_2$—$CH$=$CH_2$.

10. The compound of claim 8, wherein $R^2$ is —$CH_2$—$CH_3$.

11. A composition comprising the compound of claim 2 and a pharmaceutically acceptable carrier, excipient, or diluent.

12. A method of treatment comprising administering a therapeutically effective amount of the compound of claim 2 to a subject having a cancer mediated by an up-regulation of Hedgehog signaling wherein the cancer is basal cell carcinoma or medulloblastoma.

13. The method of claim 12 wherein the up-regulation of Hedgehog signaling is an up-regulation of Smoothened.

14. A method of synthesizing the compound of formula I of claim 1 comprising
contacting a compound of formula II-A

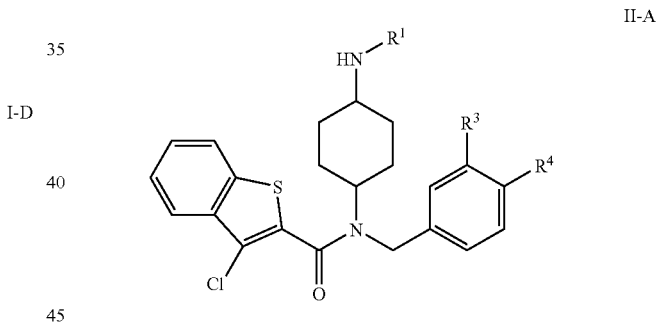

with a base and $R^2$—Z, wherein $R^1$ is an N-protecting group and
Z is a leaving group, to provide the compound of formula I

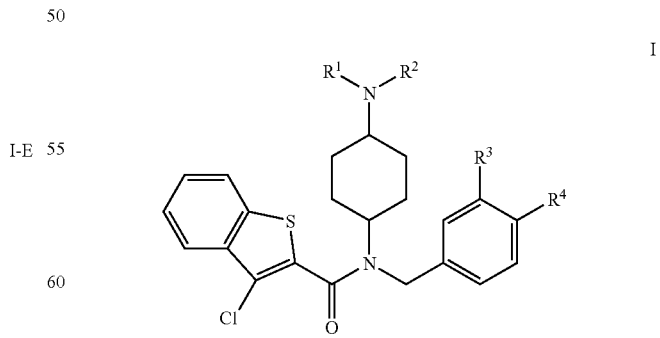

wherein $R^1$ is an N-protecting group and $R^2$, $R^3$, and $R^4$ are as defined in claim 1.

15. The method of claim 14, wherein $R^2$ is —$CH_2$—$CH_3$, $CH_2$—$CH_2$—$CH_3$, or —$CH_2$—$CH$=$CH_2$.

16. The method of claim 14, wherein the N-protecting group is t-butyloxycarbonyl, Cbz, pivaloyl, acetyl, or benzyl.

17. The method of claim 14, wherein the base is a hydride.

18. The method of claim 14 further comprising removing the N-protecting group to provide the compound of formula I wherein $R^1$ is hydrogen.

19. The method of claim 18, wherein the N-protecting group is removed by contacting the compound of formula I with an acid selected from HCl and $CF_3CO_2H$.

* * * * *